(12) United States Patent
Marcarian

(10) Patent No.: US 11,557,073 B2
(45) Date of Patent: Jan. 17, 2023

(54) SYSTEM FOR GENERATING MEDICAL DIAGNOSTIC IMAGES

(71) Applicant: PRECISION BIOMETRICS INC., Seattle, WA (US)

(72) Inventor: David Marcarian, Seattle, WA (US)

(73) Assignee: Precision Biometrics, Inc., Seattle, WA (US)

( * ) Notice: Subject to any disclaimer, the term of this patent is extended or adjusted under 35 U.S.C. 154(b) by 299 days.

(21) Appl. No.: 13/830,512

(22) Filed: Mar. 14, 2013

(65) Prior Publication Data

US 2013/0201213 A1 Aug. 8, 2013

Related U.S. Application Data

(63) Continuation-in-part of application No. 12/455,385, filed on Jun. 1, 2009, now Pat. No. 9,808,172.

(Continued)

(51) Int. Cl.
 *G06T 11/60* (2006.01)
 *A61B 5/00* (2006.01)
(Continued)

(52) U.S. Cl.
 CPC ............ *G06T 11/60* (2013.01); *A61B 5/1121* (2013.01); *A61B 5/389* (2021.01); *A61B 5/4561* (2013.01);
(Continued)

(58) Field of Classification Search
 CPC .............. G06Q 50/22–24; G06Q 50/24; G06F 19/322–327; G06F 19/321; G16H 10/00;
(Continued)

(56) References Cited

U.S. PATENT DOCUMENTS

| 4,320,767 A | 3/1982 | Villa-Real |
| 4,492,029 A | 1/1985 | Tanaka et al. |

(Continued)

FOREIGN PATENT DOCUMENTS

| EP | 1516587 A2 | 3/2005 |
| JP | 2002-502274 A | 1/2002 |

(Continued)

OTHER PUBLICATIONS

Official Communication for Chinese Patent Application No. 200980120464.3 dated Dec. 16, 2013.

(Continued)

*Primary Examiner* — Robert W Morgan
*Assistant Examiner* — Edward B Winston, III
(74) *Attorney, Agent, or Firm* — John W. Branch; Branch Partners PLLC

(57) ABSTRACT

Medical diagnostic images that are embedded with contact messages about a professional are sent to a patient for sharing with others. Although the images may be obtained using any of a variety of imaging devices, in some instances, the images may be obtained using a soft-tissue-injury diagnostic system for diagnosing soft tissue injury within a patient. A visual display is configured and arranged for receiving and displaying the medical diagnostic image. Personalized contact messages are then embedded within the image as a watermark to with information about the professional, such as an electronic business card, contact information, or hyperlinks to additional information. The sharable image with embedded messages is electronically sent to the patient for sharing with others. Personalized contact messages may also be embedded in non-medical images for sharing with others.

20 Claims, 16 Drawing Sheets

Related U.S. Application Data

(60) Provisional application No. 61/058,160, filed on Jun. 2, 2008.

(51) Int. Cl.
*A61B 5/11* (2006.01)
*A61B 5/389* (2021.01)

(52) U.S. Cl.
CPC .......... *A61B 5/6823* (2013.01); *A61B 5/6825* (2013.01); *A61B 5/743* (2013.01); *A61B 5/4528* (2013.01); *A61B 2562/0219* (2013.01)

(58) Field of Classification Search
CPC ........ G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/20; A61B 5/0536; A61B 5/1071

See application file for complete search history.

(56) References Cited

U.S. PATENT DOCUMENTS

| | | | |
|---|---|---|---|
| 4,664,130 | A | 5/1987 | Gracovetsky |
| 5,299,572 | A | 4/1994 | Chen et al. |
| 5,373,858 | A * | 12/1994 | Rose .................. A61B 5/1121 600/595 |
| 5,459,676 | A | 10/1995 | Livingston |
| 5,462,065 | A | 10/1995 | Cusimano |
| 5,513,651 | A | 5/1996 | Cusimano et al. |
| 5,588,444 | A | 12/1996 | Petragallo |
| 5,758,658 | A | 6/1998 | Petragallo |
| 5,792,077 | A * | 8/1998 | Gomes ................ A61B 5/1071 600/595 |
| 5,919,148 | A * | 7/1999 | Marko ................ A61B 5/1071 600/595 |
| 6,004,312 | A | 12/1999 | Finneran et al. |
| 6,152,954 | A * | 11/2000 | Scheiner ............ A61N 1/0573 607/123 |
| 6,364,849 | B1 | 4/2002 | Wilcox |
| 6,468,265 | B1 * | 10/2002 | Evans .................... A61B 34/35 606/1 |
| 6,823,212 | B2 | 11/2004 | Pinyayev |
| 6,856,833 | B2 | 2/2005 | Finneran et al. |
| 7,027,633 | B2 * | 4/2006 | Foran .................... G16H 80/00 128/920 |
| 7,261,693 | B2 | 8/2007 | Wilcox et al. |
| 8,059,815 | B2 * | 11/2011 | Lofgren et al. ............... 380/201 |
| 8,323,190 | B2 | 12/2012 | Vitiello et al. |
| 2002/0133094 | A1 | 9/2002 | Wilcox et al. |
| 2003/0135129 | A1 | 7/2003 | Cusimano et al. |
| 2004/0236221 | A1 | 11/2004 | Wilcox et al. |
| 2005/0075578 | A1 | 4/2005 | Gharib et al. |
| 2006/0052720 | A1 | 3/2006 | Ross et al. |
| 2006/0058699 | A1 | 3/2006 | Vitiello et al. |
| 2006/0085049 | A1 * | 4/2006 | Cory .................... A61B 5/4041 607/48 |
| 2007/0156049 | A1 | 7/2007 | Wilcox et al. |
| 2007/0167801 | A1 * | 7/2007 | Webler .................... G06T 19/00 600/459 |
| 2007/0167859 | A1 | 7/2007 | Finneran et al. |
| 2007/0208279 | A1 | 9/2007 | Panella et al. |
| 2009/0005709 | A1 | 1/2009 | Gagne |
| 2009/0281408 | A1 * | 11/2009 | Lee ....................... A61B 5/0408 600/372 |
| 2009/0299210 | A1 | 12/2009 | Marcarian |
| 2010/0168593 | A1 * | 7/2010 | Sakoda .............. A61B 5/02438 600/509 |
| 2011/0087651 | A1 * | 4/2011 | Westin et al. ................. 707/722 |
| 2012/0095779 | A1 * | 4/2012 | Wengrovitz ........... G16H 10/60 705/3 |
| 2013/0182007 | A1 * | 7/2013 | Syeda-Mahmood .. G16H 30/40 345/629 |

FOREIGN PATENT DOCUMENTS

| | | |
|---|---|---|
| JP | 2004-187736 A | 7/2004 |
| JP | 2007-209608 A | 8/2007 |
| WO | 0137728 A1 | 5/2001 |

OTHER PUBLICATIONS

International Search Report and Written Opinion for International Patent Application No. PCT/US2009/045828 dated Jan. 14, 2010.
International Preliminary Report on Patentability for International Patent Application No. PCT/US2009/045828 dated Dec. 16, 2010.
Official Communication for Australian Patent Application No. 2009256441, dated Feb. 28, 2013.
Official Communication for Australian Patent Application No. 2009256441, dated May 28, 2012.
Official Communication for Chinese Patent Application No. 200980120464.3 dated May 23, 2013.
Official Communication for European Patent Application No. 09759169.7, dated May 13, 2013.
Official Communication for Korean Patent Application No. 10-2010-7029868 dated May 15, 2013.
"MES 9000 Musculoskeletal Evaluation System," NOROMED, Mar. 2002, XP002712409 http://web.archive.org/web/20070221072403/http://www.noromed.com/myotronics_root/uploadedfiles/MES%209000%20Brocue1.pdf.
Search Report for European Patent Application No. 13181241.4-1660 dated Sep. 23, 2013.
Official Communication for Japanese Patent Application No. 2011-512562 dated Aug. 7, 2013.
Office Communication for JP Application 2013-231408 dated Sep. 24, 2014 (4 pages).
Official Communication for U.S. Appl. No. 12/455,385 dated Dec. 19, 2013.
Noromed. Aug. 23, 2011, Brochure published 2002, device cleared by FDA 2001; http://www.noromed.com.
"Static SEMG Testing Procedure," 2007, Spinal Resources, Aug. 23, 2011; http://spinalresources.com/html/static__semg__testing.html.
Joines, S.M.B. et al., "Low-level Exertions of the Neck Musculature: A Study of Research Methods," Journal of Electromyography and Kinesiology, 2006, vol. 16, pp. 485-497.
Geisser, M.E. et al., "A Meta-Analytic Review of Surface Electromyography Among Persons with Low Back Pain and Normal, Healthy Controls," The Journal of Pain, 2005, vol. 6, No. 11, pp. 711-726.
Wimalaratna, H.S.K. et al., "Quantitative Surface EMG in the Diagnosis of Neuromuscular Disorders," Electromyography and Clinical Neurophysiology, 2002, vol. 42, pp. 167-174.
European Search Report, Application No. EP 09759169, dated Oct. 15, 2012.
Official Communication for Chinese Patent Application No. 200980120464.3 dated May 3, 2012.
Official Communication for Chinese Patent Application No. 200980120464.3 dated Oct. 17, 2012.
Official Communication for Korean Patent Application No. 10-2010-7029868 dated Aug. 17, 2012.
Official Communication for Korean Patent Application No. 10-2010-7029868 dated Feb. 27, 2013.
Official Communication for U.S. Appl. No. 12/455,385 dated Aug. 29, 2011.
Official Communication for U.S. Appl. No. 12/455,385 dated Feb. 15, 2012.
Official Communication for U.S. Appl. No. 12/455,385 dated Apr. 17, 2012.
Office Communication for U.S. Appl. No. 12/455,385 dated Aug. 20, 2015 (32 pages).
Examination Report for UK Patent Application No. 1404323.6 dated Mar. 20, 2020, pp. 1-5.

* cited by examiner

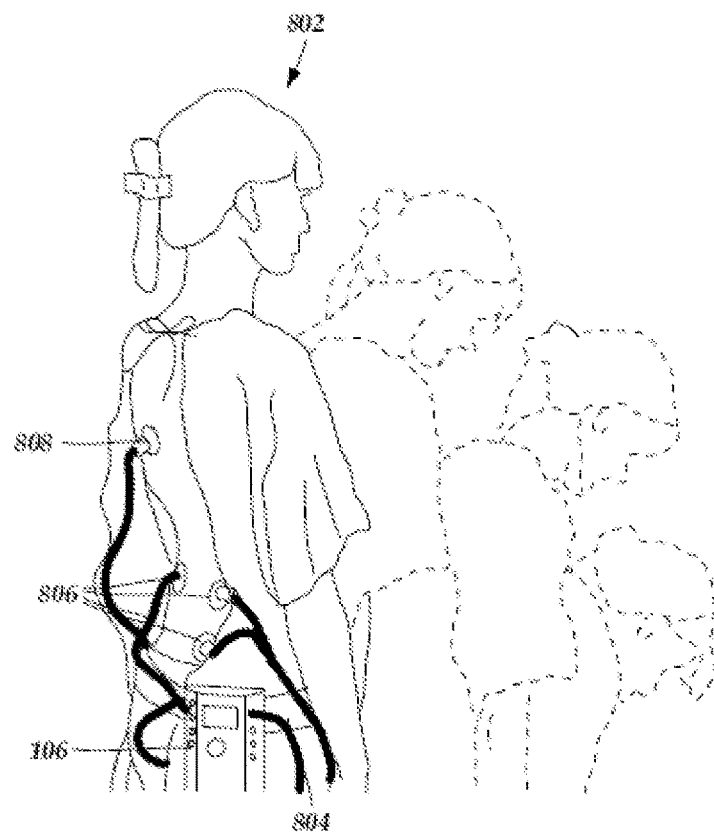
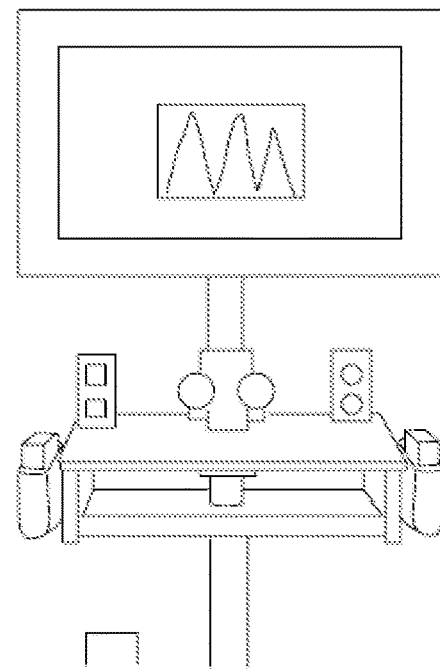
Fig. 8
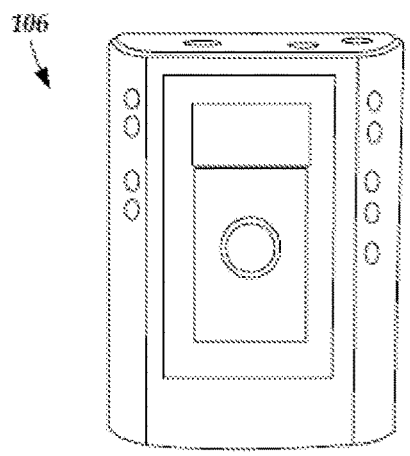
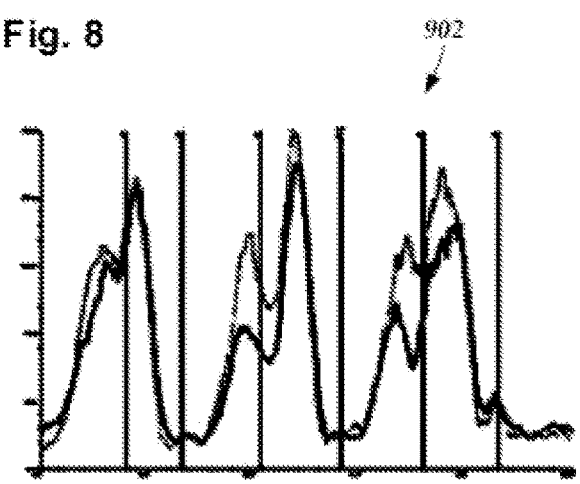
Fig. 9
Fig. 7

SYSTEM FOR GENERATING MEDICAL DIAGNOSTIC IMAGES

CROSS-REFERENCE TO RELATED APPLICATIONS

This application is a continuation-in-part patent application of U.S. patent application Ser. No. 12/455,385, entitled "Systems and methods for performing surface electromyography and range-of-motion tests," filed on Jun. 1, 2009, which in turn is based on a previously filed U.S. Provisional Patent Application Ser. No. 61/058,160 filed on Jun. 2, 2008, where the benefit of each is hereby claimed at least under 35 U.S.C. §§ 120 and 119(e) and the disclosures of which are herein incorporated by reference in their entirety.

TECHNICAL FIELD

The present embodiments are directed generally to communicating contact messages within medical diagnostic images, and more particularly, but not exclusively, to generating contact messages, such as electronic business cards, promotions, or the like, that are embedded within medical diagnostic images for transmitting to a person's computing device, which in turn may be shared by the person with others.

BACKGROUND

Diagnosing soft-tissue injuries (e.g., injury to tissues that connect, support, or surround structures and organs of the body including, for example, muscles, tendons, ligaments, fascia, nerves, fibrous tissue, fat, blood vessels, synovial tissues, and the like), as well as assessing pain associated with soft-tissue injury, may be difficult. Soft tissue injuries are often not viewable by the naked eye. Additionally, soft-tissue injury may be difficult (and expensive) to assess even with medical imaging techniques, such as magnetic resonance imaging, computed tomography, ultrasound, and the like. Moreover, the resulting medical images may be difficult for a patient or prospective patient to understand or explain to others.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7 is a schematic front view of one embodiment of an sEMG module of the soft-tissue-injury diagnostic system shown in FIG. 1, according to the invention;

FIG. 8 is a schematic view of the dynamic sEMG module shown in FIG. 7 coupled to a patient via measuring electrodes while a dynamic sEMG test is performed on the patient, according to the invention;

FIG. 9 is a schematic view of one embodiment of an exemplary result of a dynamic sEMG test performed on a patient, according to the invention;

FIG. 25 illustrates a logical flow diagram generally showing one embodiment of a process usable to generate and transmit one or more contact messages embedded within a medical diagnostic image; and.

DETAILED DESCRIPTION

Figure 1:
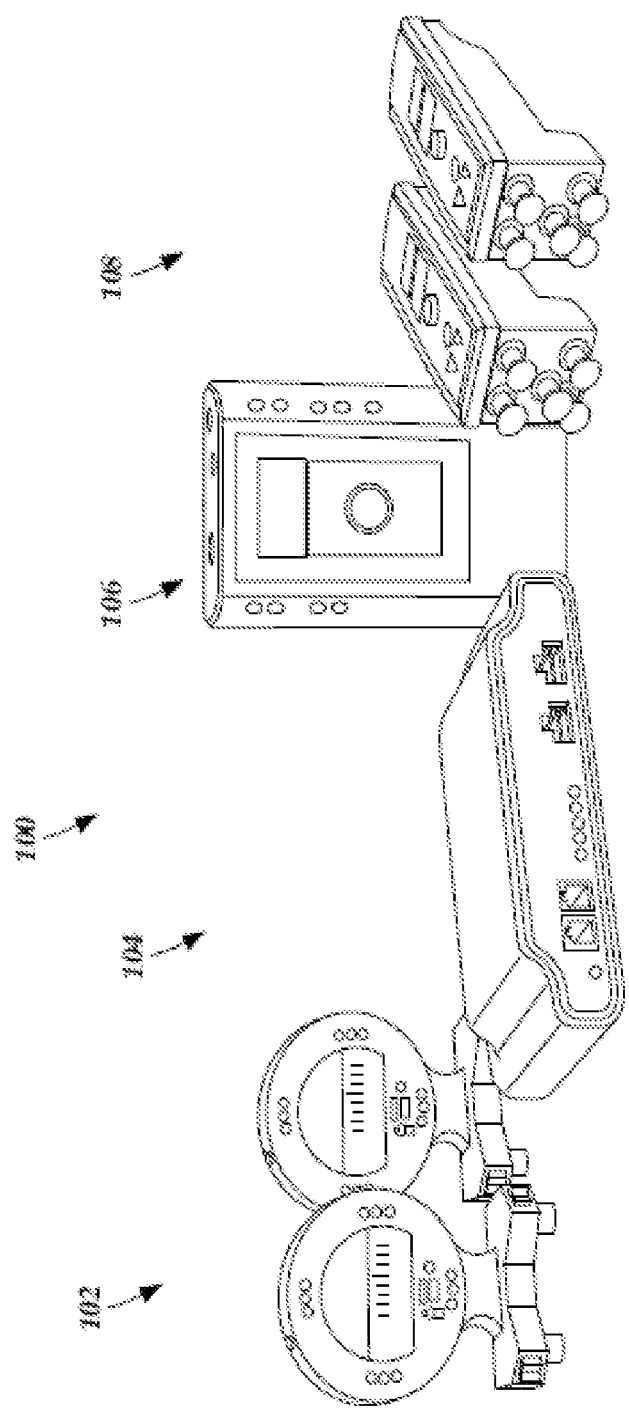
FIG. 1 is a schematic perspective view of one embodiment of a soft-tissue-injury diagnostic system, according to the invention.

The present invention is directed to medical diagnostic instrumentation. The present invention is also directed to systems and methods for evaluating soft-tissue-injury using surface electromyography or range-of-motion testing separately or in combination with one another. The present invention is further directed towards providing devices, methods, systems, and non-transitory computer-readable devices usable to generate contact messages, such as electronic business cards, that are embedded within personalized medical diagnostic images, or other images, for transmitting to a person's computing device. One embodiment of such images may be obtained from the herein disclosed soft-tissue-injury diagnostic system for diagnosing soft tissue injury within a patient. In one embodiment, the disclosed diagnostic system includes a set of hand-held inclinometers configured and arranged for measuring angles formed between a first inclinometer disposed in proximity to a patient joint and a second inclinometer disposed distal to the joint during controlled patient movements of the joint. A plurality of measuring electrodes is coupleable in proximity to the patient's spine along the body portion that moves along the joint. The measuring electrodes are configured and arranged for measuring action potentials along patient muscle groups during the controlled patient movements of the joint and transmitting the measured action potentials to a dynamic surface electromyograph ("sEMG") module. Other embodiments for generating a diagnostic visual image might include using a plurality of electrodes which are held against the patient's body for a measurement of action potentials while the patient is in a neutral posture" A hub as described below may then receive and processes data from the inclinometers, dynamic sEMG module and the Static sEMG module. A visual display is configured and arranged for receiving and displaying the processed data. The processed data may include at least one diagnostic image that may then be embedded with various contact messages disclosed further below. In one embodiment, an embedded contact message may include hyperlinks, or other mechanisms, usable by a recipient to contact a medical professional for follow-up medical care. The image with the embedded contact message may be sent via email or other methods to the patient, who may subsequently share the image and contact message with others, including posting the image and contact message on a social network site, emailing to others, or the like.

The methods, systems, and devices described herein may be embodied in many different forms and should not be construed as limited to the embodiments set forth herein. Accordingly, the methods, systems, and devices described herein may take the form of an entirely different hardware embodiment, an entirely different software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of non-transitory computer storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other non-transitory medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Over the years, several types of medical diagnostic devices have been developed that measure one or more patient capabilities which may be helpful in evaluating soft-tissue injury. One such type of medical diagnostic device is a surface electromyograph ("sEMG"), which can be used for measuring the muscle tension of selected muscle groups of a patient, either while the patient performs various movements (e.g., a dynamic sEMG) or while a patient is at rest (e.g., a static sEMG). Another such type of medical diagnostic device is a range-of-motion tester ("ROM"), which can be used for measuring how far a patient can bend along a given joint. However, despite advancements in sEMG and ROM technologies, a tool for completely diagnosing soft-tissue injuries and assessing corresponding patient pain remains elusive.

As a result of the inability to reliably diagnose or assess soft-tissue injury, the healthcare system may experience a financial burden by misdiagnosing some types of patient injuries and consequently applying inappropriate therapies. Additionally, the insurance system and the court system may likewise experience a financial burden due to some people falsely claiming (or grossly exaggerating the extent of) soft-tissue injuries in order to receive money or other forms of consideration.

Moreover, many medical professionals have found that patients, and/or their relatives find it difficult to understand results of various diagnostic tools, let alone are able to explain the results, or a need for follow-up care, to others. This complexity has sometimes resulted in a patient not returning for follow-up care, or potential patients not becoming a patient at all. Therefore, many medial professionals have tried various methods to assist patients, and potential patients, in better understanding their medical diagnosis, and benefits of a follow-up session. Some professionals have even tried high paid endorsements, various marketing schemes, and other approaches to educate the public, and to reach new patients.

As disclosed herein various embodiments are directed towards these issues, as well as others, by providing for personalized contact messages that have visual objective and personalized data validating for a patient, a diagnostic result. Moreover, embodiments disclosed herein provide for electronically sending to the patient contact messages, including for example, electronic business cards, advertisements, coupons, or the like, that are embedded into a personalized medical diagnostic image. Because the image is configured to exclude patient confidential information, the recipient of the image with the embedded contact messages, may post the image and messages to various social networking sites or even forward the image with the messages to their family or friends. In this way, the patient may be better able to explain their medical diagnosis, and understand 'why' they may want a follow-up session. By allowing the patient to share with others their personalized image with the embedded contact messages, the professional's practice may be marketed virally, virtually 24/7.

In some embodiments, an embedded contact message may include a hyperlink, or other mechanism, that can be used to access the professional's office to arrange for an appointment, or to learn more about their diagnostic results. In other embodiments, the contact message may include advertisements, coupons, discounts, or other information. In various embodiments, information about the patient may be obtained during an initial diagnostic session and later used, with permission, to subsequently contact the patient by the professional's office.

In at least some embodiments, a soft-tissue-injury diagnostic system ("diagnostic system") may be used to perform one or more diagnostic tests on a patient, either singularly or in combination, including an ROM test, a dynamic sEMG test, and a static sEMG test. In at least some embodiments, the diagnostic system also includes one or more video cameras. In at least some embodiments, multiple video cameras may be used to capture video (or photographs) of a patient's movements while undergoing one or more of the abovementioned tests. In at least some embodiments, results from one or more of the tests may be used by one or more medical practitioners to diagnose or assess soft-tissue injury.

While the embodiments disclosed herein are primarily directed to using a soft-tissue-injury diagnostic system to capture medical diagnostic images, it should be understood that other images may be embedded with contact messages and sent to a patient. For example, dental images, various magnetic resonance images, positron emission tomography (PET) images, or any of a variety of other medial images may also be embedded with contact messages and sent to a patient for sharing with others. In still other examples, a pharmacy, or other professional might configure images of a person's blood pressure analysis with embedded contact messages. The personalized image with the embedded contact messages may then be electronically sent to the person for sharing with their friends, family, spouses, or others, as well as posting on a social networking site.

Further, non-medial professionals might employ the embodiments herein to embed contact messages within other images that may be sent to clients for subsequent sharing with others. Thus, it should be understood that embedding of contact messages within sharable images is not constrained to merely medical images, and other systems and environments are also envisaged.

However, within a medical environment, FIG. 1 is a schematic perspective view of one embodiment of a diagnostic system 100. The diagnostic system 100 includes inclinometers 102 for performing an ROM test on a patient (testing how far the patient can bend), a hub 104, a dynamic sEMG control module ("sEMG module") 106 for use in performing a dynamic sEMG test on a patient (measuring action potentials along muscle groups as the patient performs various movements), and static sEMG scanners ("scanners") 108 for performing a static sEMG test on a patient (measuring action potentials along muscle groups as the patient maintains a given position).

In at least some embodiments, the inclinometers 102, the dynamic sEMG module 106, and the scanners 108 are in electrical communication with the hub 104. In some embodiments, one or more of the inclinometers 102, the dynamic sEMG module 106, and the scanners 108 are electrically coupled to the hub 104 by a wireless network, such as 3G. In other embodiments, one or more of the inclinometers 102, the dynamic sEMG module 106, and the scanners 108 are electrically coupled to the hub 104 by one or more conductors, such as wires.

Figure 2:
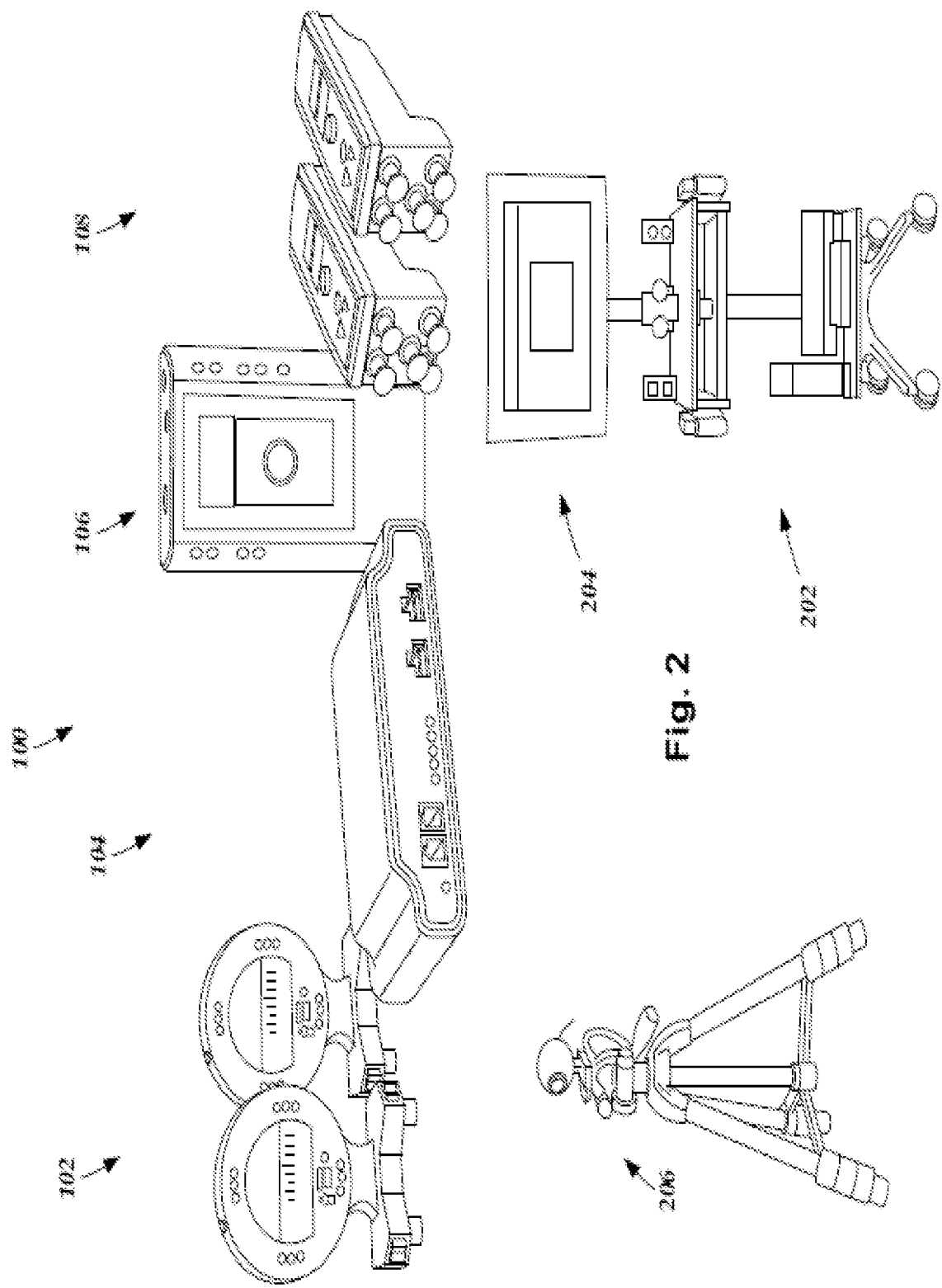
FIG. 2 is a schematic perspective view of another embodiment of the soft-tissue-injury diagnostic system shown in FIG. 1, according to the invention.

In at least some embodiments, the diagnostic system 100 also includes (as shown in FIG. 2) one or more processors 202, one or more visual displays 204, and one or more video cameras 206. In at least some embodiments, the hub 104 is electrically coupled to the one or more processors 202. In at least some embodiments, the one or more processors 202 receive and process input data from the inclinometers 102, the dynamic sEMG module 106, or the scanners 108 (via the hub 104) and display the results of the processed data on the one or more visual displays 204. In at least some embodiments, at least a portion of one or more of the ROM test, the dynamic sEMG test, or the static sEMG test are visually captured by the one or more video cameras 206.

In at least some embodiments, the diagnostic system 100 includes software or hardware for facilitating many different operations including, for example, linking the inclinometer 102, the dynamic sEMG module 106, or the scanners 108 to the hub 104, performing the ROM test, the dynamic sEMG, and the static sEMG, displaying the results of the ROM test, the dynamic sEMG, or the static sEMG, saving and backing-up testing data, and powering on or off the testing devices.

Figure 3:
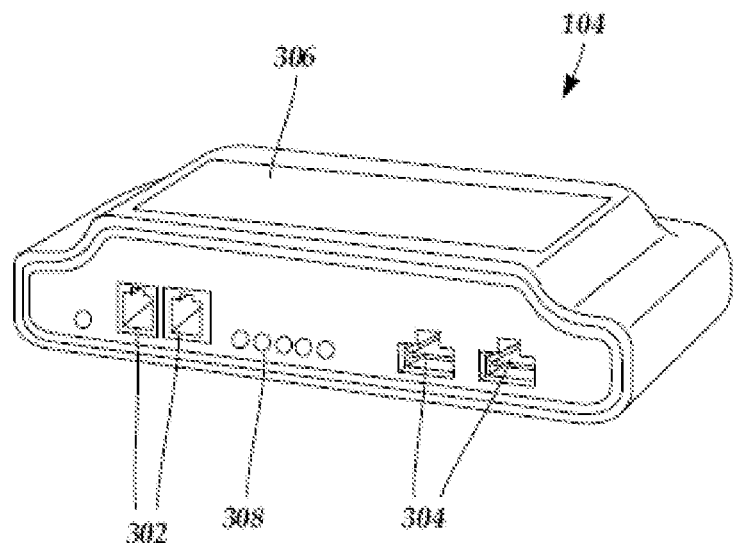
FIG. 3 is a schematic perspective view of one embodiment of a hub of the soft-tissue-injury diagnostic system shown in FIG. 1, according to the invention.

FIG. 3 is a schematic front view of the hub 104. In at least some embodiments, the hub 104 includes one or more inputs 302 for coupling the inclinometer 102, the dynamic sEMG module 106, or the scanners 108 to the hub 104. In at least some embodiments, the hub 104 also includes inputs 304 for one or more peripherals (e.g., a keyboard, a mouse, a monitor, a printer, a storage device, or the like). In at least some embodiments, the hub 104 includes one or more user interfaces 306 (e.g., displays, keypads, or the like). In at least some embodiments, the hub 104 includes one or more indicators 308, such as a power indicator, connectivity indicator, or the like. In at least some embodiments, multiple hubs 104 may be utilized, in parallel or in series. In at least some embodiments, the one or more hubs 104 receive and process input data from the inclinometers 102, the dynamic sEMG module 106, or the scanners 108 and display the results on a display, such as an LCD, coupled to (or disposed on) the hub 104. In at least some embodiments, the one or more hubs 104 include a keypad for inputting information.

Figure 4:
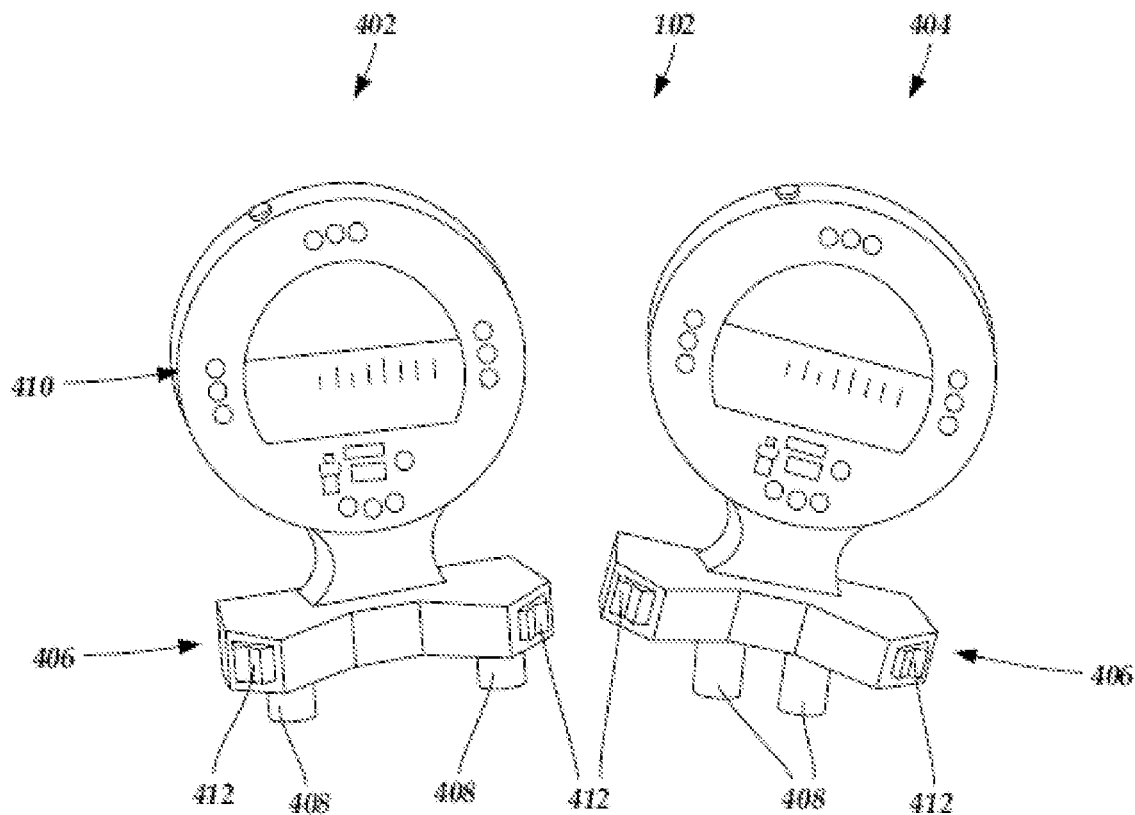
FIG. 4 is a schematic front view of one embodiment of inclinometers of the soft-tissue-injury diagnostic system shown in FIG. 1, the inclinometers including a main unit and an auxiliary unit, according to the invention.

FIG. 4 is a schematic front view of one embodiment of the inclinometers 102 of the diagnostic system 100. The inclinometers 102 include a main unit 402 and an auxiliary unit 404. In at least some embodiments, the main unit 402 and the auxiliary unit 404 are each substantially disc-shaped with a coupled flat bottom surface 406 extending tangentially from a bottom portion of the discs. In at least one embodiment, the flat bottom surface 406 includes two or more feet 408. In at least some embodiments, the feet 408 are independently slidable along the flat bottom surface 406 such that the distance between the feet 408 may be adjusted.

In at least some embodiments, the main unit 402 and the auxiliary unit 404 each include a plurality of light-emitting diodes ("LEDs"), such as LEDs 410 positioned on the bodies of the main unit 402 and the auxiliary unit 404 to form degree markings. For example, the LEDs may be positioned to mark 0 degrees, 90 degrees, 180 degrees, and 270 degrees when the main unit 402 or the auxiliary unit 404 is placed in an upright position resting on the flat bottom surface 406. In at least some embodiments, the LEDs may be used by a user to determine a relative angle between the main unit 402 and the auxiliary unit 404 without needing to look at a computer display to obtain this information. In at least some embodiments, the LEDs may be used to mark the degrees of rotation between the main unit 402 and the auxiliary unit 404 based upon gravity.

In at least some embodiments, the main unit 402 and the auxiliary unit 404 use accelerometers. By using the LED degree markings and accelerometers, a user is able to use a true level (bubble-type level) to calibrate the inclinometers 102 to true center of the earth, and then have the ability to show, with LEDs, true zero with respect to gravity.

In at least some embodiments, the LEDs allow a user to see, by looking at the main unit 402 or the auxiliary unit 404, when the main unit 402 or the auxiliary unit 404 is at various degrees from earth center zero gravity. This allows the user to electronically provide a measurement without the use of a manual visual pendulum (which is a technique currently employed by some conventional devices). This may save time, and provide a more accurate reading as the angle data is stored by the hub 104 or the one or more processors 202, and does not require a human to calculate degrees.

In at least some embodiments, one or more LED-flashing systems may be implemented to convey to a user at what angle either the main unit 402 or the auxiliary unit 404 is at during performance of an ROM test. For example, when the LEDs are configured so that one or more LEDS mark 0 degrees, 90 degrees, 180 degrees, and 270 degrees, the LED(s) may provide feedback to the user as follows: when the main unit 402 or the auxiliary unit is at 0 degrees, for example, the one or more LEDs marking 0 degrees emit a green light. When the main unit 402 or the auxiliary unit 404 is rotated to 0 degrees minus 1 degree, the one or more LEDs marking 0 degrees emit a yellow light and flash at a rate of 1 time per second. When the main unit 402 or the auxiliary unit 404 are rotated to 0 degrees minus 2 degrees, the one or more LEDs marking 0 degrees emit a yellow light and flash at a rate of 2 times per second. In at least some embodiments, this continues on up to 5 degrees. When the main unit 402 or the auxiliary unit 404 are rotated to 0 degrees plus 1 degree, the one or more LEDs marking 0 degrees emit a red light or another color, and will flash with the same frequency as above, increasing at the same rate as the number of degrees increases from zero. So, for example, at 5 degrees, the one or more LEDs marking 0 degrees emit a red light and flash at a rate of 5 times per second.

In other embodiments, the main unit 402 or the auxiliary unit 404 each include 11 LEDs. In at least some embodiments, a plurality of colors are used. For example, the center may include 1 green LED. On either side at 1 degree increments there may be yellow LED's which indicate 1 degree increments under 0 degrees. On the other side of the 1 green LED there may be 5 red (or another color) LEDs which are spaced equally by 1 degree, and light up in order from the 1st to 5th LED indicating 1 to 5 degrees from center (0 degrees in this case). The 1 green LED in the center may emit light when the main unit 402 or the auxiliary unit 404 is held at 0 degrees compared to earth, and as the main unit 402 or the auxiliary unit 404 is moved away from 0 degrees (or any of the major markers (typically 0, 90, 180, 270), with the LED's lighting up in order as the 1-5 degrees is met from center.

In at least some embodiments, software associated with the ROM test utilizes voice signaling to facilitate operation of the inclinometers 102 or performance of an ROM test. For example, a voice signal may be output, via one or more speakers electrically coupled to the hub 104 or the one or more processors 202, the actual level in degrees in comparison to the center of the earth for one or both of the units 402 and 404 so that a user can focus on holding the main unit 402 or the auxiliary unit 404 against the patient and provide a more accurate reading, without dividing attention to attempt to read the values on a screen or on a mechanical device.

For example, when the main unit 402 or the auxiliary unit 404 is set up so that the top is at 0 degrees (is straight up and down), a voice signal may be emitted that says "zero degrees." In addition, the emitted voice signal may say "plus 1 degree," "plus two degrees," or the like, to mark the movement of the main unit 402 or the auxiliary unit 404 from center position. In at least some embodiments, voice signaling may be used to provide commands to a user of the inclinometers 102 before, during, or after a ROM test. For example, a voice signal may prompt the user when to instruct a patient to perform a given movement, when to record a marking (discussed below), or the like.

In at least some embodiments, the inclinometers 102 include one or more controllers 412 (e.g., buttons, switches, knobs, or the like) that may be used by a user during an ROM test to record a marking. For example, in at least some embodiments, the user may press a button during an ROM test to record a marking when a patient is at a neutral position, or when a patient is at a fully-flexed position. The recorded markings may be subsequently used to facilitate interpretation of a display of results from the ROM test. In at least some embodiments, two controllers 412 are positioned on each of the inclinometers 102. In at least some embodiments, the inclinometers 102 can be operated using either of the two controllers 412.

In at least some embodiments, the inclinometers 102 are powered by one or more batteries. In at least some embodiments, the inclinometers are automatically powered off after a given amount of time has elapsed without being used. In at least some embodiments, the inclinometers 102 are automatically powered off after the associated software has been powered off. In at least some embodiments, the inclinometers 102 are automatically powered off after an ROM test has been completed. In at least some embodiments, the inclinometers 102 include a master power switch which, when in one position, maintain the inclinometers 102 powered off.

In at least some embodiments, the inclinometer 102 is in electrical communication with the hub 104 and data created during the performance of an ROM test are input to the hub 104. In at least some embodiments, the data is processed by the hub 104 (or a plurality of hubs). In at least some embodiments, at least some of the data input to the hub 104 is output to the one or more electrically coupled processors 202 for further processing.

In at least some embodiments, the inclinometers 102 are positioned along a patient body portion that moves along a patient joint at one end of the body portion. The body portion can be any part(s) of the body, such as a limb, extending distally from a joint (e.g., head, neck, finger, hand, arm, forearm, waist, toe, ankle, knee, leg, or the like or combinations thereof). The inclinometers 102 may be positioned such that the main unit 402 is positioned against a patient joint and the auxiliary unit 404 is positioned distally from the joint along the moveable body portion.

Figure 5:
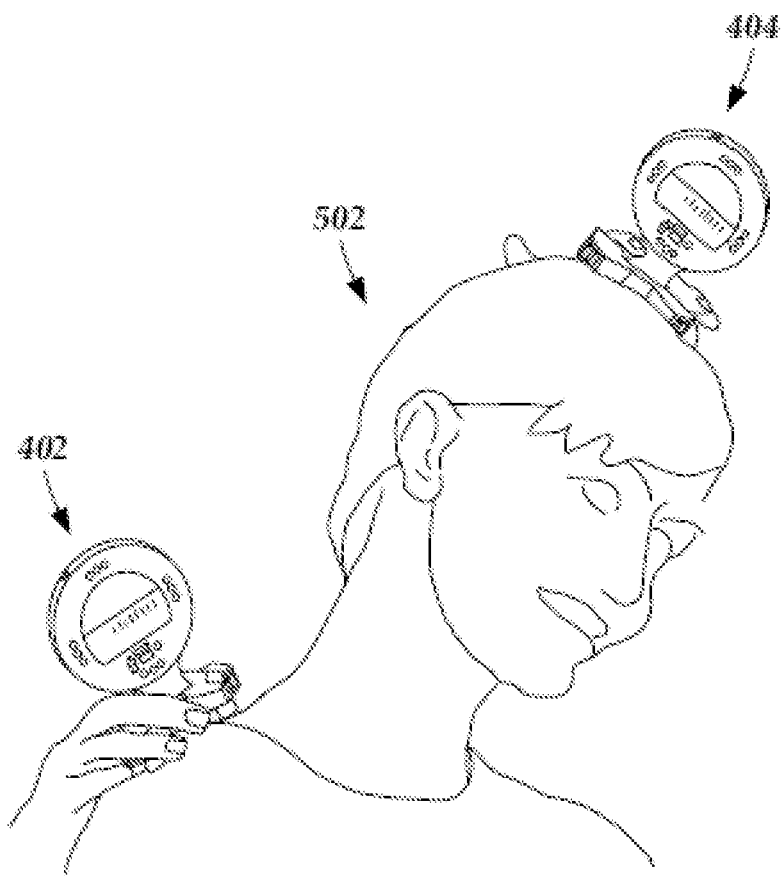
FIG. 5 is a schematic view of one embodiment of the inclinometers shown in FIG. 4 being used by a user to perform an ROM test on a patient, according to the invention.

FIG. 5 is a schematic view of one embodiment of the inclinometers 102 being used to perform an ROM test on a patient 502. In FIG. 5, a lateral flexion ROM test is being performed on the patient's cervical spine. It will be understood that this is just one of many different ROM tests that may be performed on a patient 502. In FIG. 5, the main unit 402 is positioned at the base of the neck, for example, and the auxiliary unit 404 on top of the head, a difference between the main unit 402 and the auxiliary unit 404 (in degrees compared with zero gravity ground) is measured as the patient moves from a neutral position to a fully-flexed position in a given direction (e.g., laterally flexed). As the patient 502 bends his or her head laterally, the difference between the two units 402 and 404 in degrees (main unit 402 minus auxiliary unit 404) provides the actual number of degrees which the patient 502 has flexed his or her neck. The main unit 402 and the auxiliary unit 404 may, therefore, be used to measure the range of motion as the hub 104 (or one or more coupled processors 202) is able to quickly and accurately measure both the main unit 402 and the auxiliary unit 404 simultaneously to measure the angle of movement. In at least some embodiments, the associated software remains idle until the patient 502 is in a final neutral posture.

In at least some embodiments, the feet 408 on the main unit 402 or the auxiliary unit 404 are adjustable. In at least some embodiments, at least one of the feet 408 slides along an axis separating the feet 408 (e.g., along an axis of the flat bottom surface 406), thereby increasing or decreasing the distance between the feet 408. In at least some embodiments, the adjustable feet 408 may be used to facilitate steady contact being made between the main unit 402 or the auxiliary unit 404 and the patient. For example, it may be the case that measuring the range of motion of one of the patient's fingers is more easily performed when the feet 408 are closer together than when measuring the range of motion of the patient's waist.

In at least some embodiments, the shape of the main unit 402 and the auxiliary unit 404 may also facilitate making steady contact with a patient. In at least some embodiments, a user may place hold of the main unit 402 or the auxiliary unit 404 between two of his or her fingers with his or her palm flat against the patient (as shown in FIG. 5) so as to steadily hold the main unit 402 or the auxiliary unit 404 in position while still being able to see the LEDs and use the control buttons 412 during performance of an ROM test.

Figure 6:
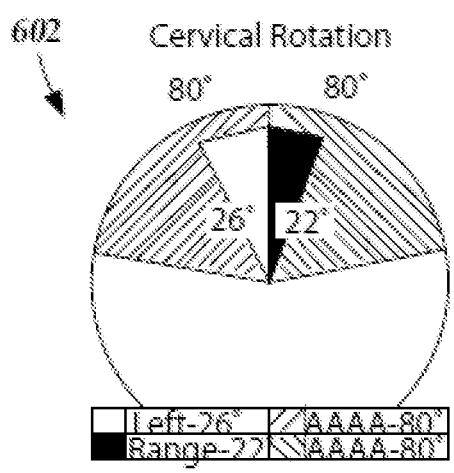
FIG. 6 is a schematic view of one embodiment of an exemplary result for an ROM test performed on a patient and displayable on a visual display, according to the invention.

FIG. 6 is a schematic view of one embodiment of an exemplary display 602 for an ROM test performed on the patient 502 and displayable on the one or more visual displays 204. Note that the exemplary display 602 of a ROM test can be displayed in many other different ways on the one or more visual displays 204. In at least some embodiments, the display 602 can be displayed on the hub 104 or other display electrically coupled to the hub 104 in lieu of, or in addition to, the one or more visual displays 204.

FIG. 7 is a schematic front view of one embodiment of the dynamic sEMG module 106 of the diagnostic system 100. In at least some embodiments, the dynamic sEMG module 106 is configured and arranged for facilitating the performance of a dynamic sEMG test on a patient. In at least some embodiments, data collected during performance of the dynamic sEMG test is input to the hub 104 and processed by the hub 104 or by one or more processors 202. In at least some embodiments, the dynamic sEMG module 106 includes a master power switch (not shown) which, when in one position, maintain the dynamic sEMG module 106 powered off.

In at least some embodiments, the dynamic sEMG module 106 is configured and arranged to receive measuring electrodes coupled to a patient. In at least some embodiments, the dynamic sEMG module 106 is configured and arranged to receive up to sixteen measuring electrodes. The measuring electrodes coupled to the dynamic sEMG module 106 may be formed from many different conductive materials suitable for placement against the skin of a patient including, for example, gold, stainless steel, silver, silver chloride, and the like or combinations thereof. In at least some embodiments, multiple dynamic sEMG modules may be electrically coupled to one another or to the hub 104.

FIG. 8 is a schematic view of a patient 802 performing a movement associated with a dynamic sEMG test. In FIG. 8, the dynamic sEMG module 106 is coupled to a strap 804 (e.g., a belt, or the like) being worn by the patient 802. In at least some embodiments, measuring electrodes 806 are attached to the patient 802 and electrically coupled to the dynamic sEMG module 106. The measuring electrodes 806 are positioned at various spinal levels determined by the muscle groups whose activity is to be measured during controlled patient movement. For example, the measuring electrodes 806 may be attached to the back of the patient 802 in lateral proximity to the spine at various spinal levels to measure the size and timing of action potentials as the patient moves in a manner that utilizes the muscles in proximity to the location of the attached measuring electrodes 806. In at least some embodiments, a ground 808 may also be used to couple the patient 802 to the dynamic sEMG module 106.

In FIG. 8, the patient 802 has measuring electrodes 806 attached to her back which measure the size and timing of action potentials along selected muscle groups during flexion and extension at her waist. In at least some embodiments, multiple dynamic sEMG modules 106 (each dynamic sEMG module 106 electrically coupled to multiple different measuring electrodes) may be used to perform multiple concurrent dynamic sEMG tests on a patient. In at least some embodiments, when multiple dynamic sEMG tests are performed on a patient, multiple results may be input to the hub 104.

FIG. 9 is a schematic view of one embodiment of an exemplary display 902 of a dynamic sEMG test performed on the patient 802. Note that exemplary display 902 of a dynamic sEMG test can be displayed in many other different ways on the one or more visual displays 204. In at least some embodiments, the exemplary display 902 is displayed on the hub 104 or a visual display electrically coupled to the hub 104.

Figure 10:
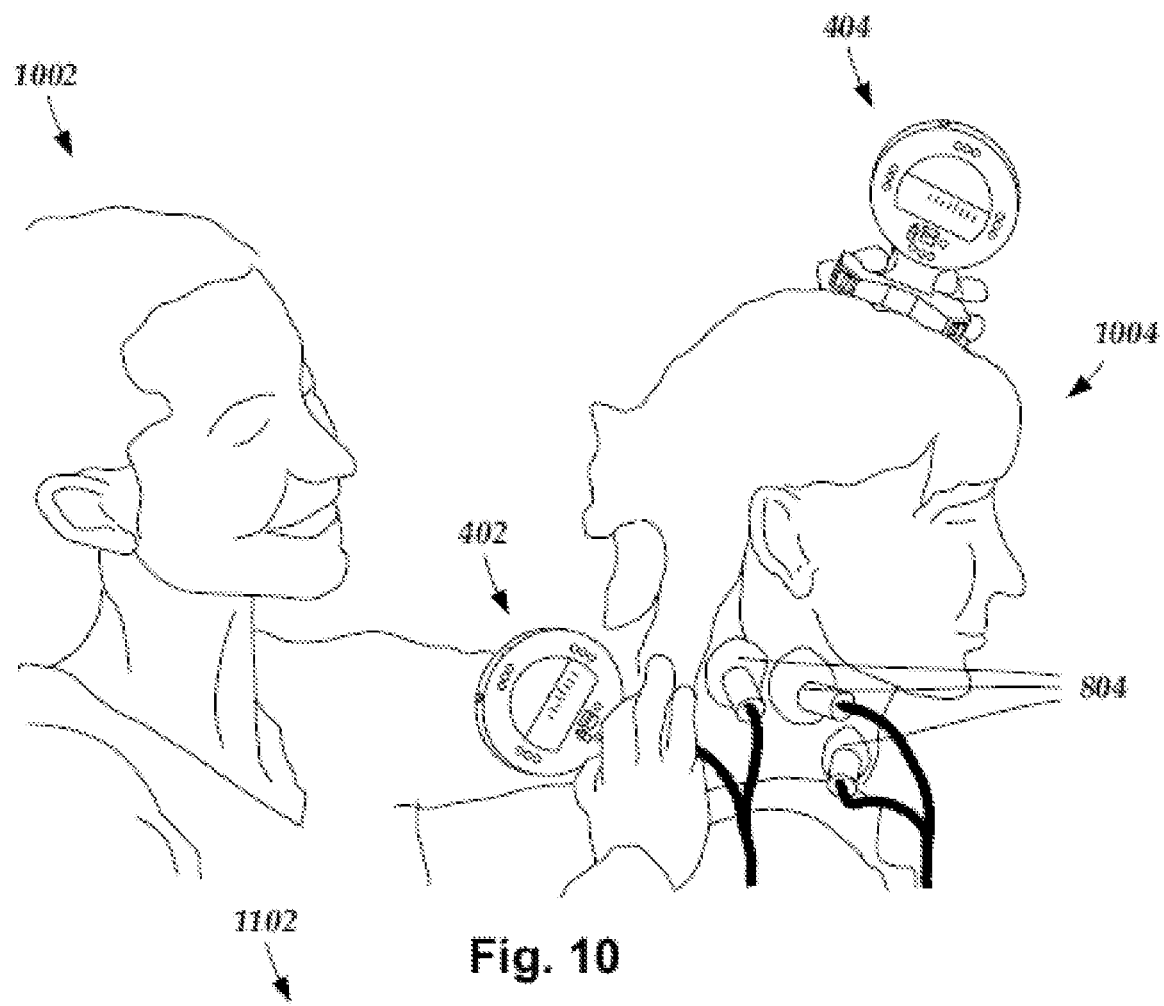
FIG. 10 is a schematic view of one embodiment of the inclinometers shown in FIG. 4 and the dynamic sEMG module shown in FIG. 7 being used to concurrently perform an ROM test and a dynamic sEMG test on a patient, according to the invention.

In at least some embodiments, an ROM test and one or more dynamic sEMG tests may be performed concurrently. FIG. 10 is a schematic view of one embodiment of a user 1002 concurrently performing an ROM test and a dynamic sEMG test on a patient 1004. The inclinometers 102 (ROM test) and the measuring electrodes 806 of the dynamic sEMG module 106 (dynamic sEMG test) are shown coupled to the patient 1004. In at least some embodiments, measuring muscle activity and range of motion concurrently may provide further insight into the nature and extent of patient injury. In at least some embodiments, data from both the ROM test and the dynamic sEMG test may be combined together in a single graphic display to show the timing, symmetry, and magnitude of the patient's muscle responses during patient movement. In at least some embodiments, combining an ROM test with a dynamic sEMG test may increase the accuracy of readings and also create results with increased reproducibility from conventional tests.

In at least some embodiments, the data for one or more of the motions from the ROM test may be arranged in a graphic which follows the American Medical Association ("AMA") guides for ROM, such as the pie graph result 602 shown in FIG. 6. Currently, the only known method to gather ROM data and generate impairment ratings based upon the AMA guides is to perform the ROM test separately from the dynamic sEMG. By performing the ROM test and dynamic sEMG tests concurrently and generating ROM data in the format required by the AMA guides, time and money may be saved. In at least some embodiments, when ROM data, after a selected number of trials of each motion, is not within the required variability allowed by the AMA guides, the software automatically informs the user that the ROM test in invalid, and may be performed again, thereby potentially saving additional time and money.

Figure 11:
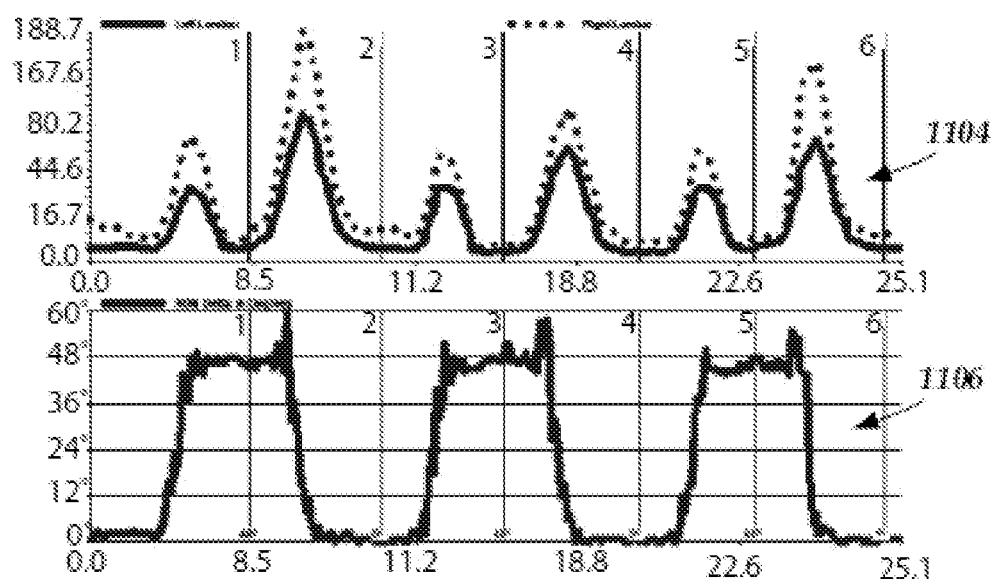
FIG. 11 is a schematic view of one embodiment of an exemplary result for an ROM test and a dynamic sEMG test performed concurrently on a patient and displayable together on a visual display, according to the invention.

FIG. 11 is a schematic view of one embodiment of an exemplary visual display 1102 showing results of a concurrently performed ROM test and dynamic sEMG test. In FIG. 11, the dynamic sEMG data 1104 is shown graphically on the top half of the visual display 1102 and the ROM data 1106 is shown graphically on the bottom half of the visual display 1102. The dynamic sEMG data 1104 and the ROM data 1106 are shown over time so that muscular activity of selected muscles can be seen visually during a corresponding performance of specific movements by the patient 1004. In at least some embodiments, timing, symmetry, and magnitude of the patient's muscle responses may be displayed. In at least some embodiments, such information may correspond with the nature and extent of patient injury.

Figure 12:
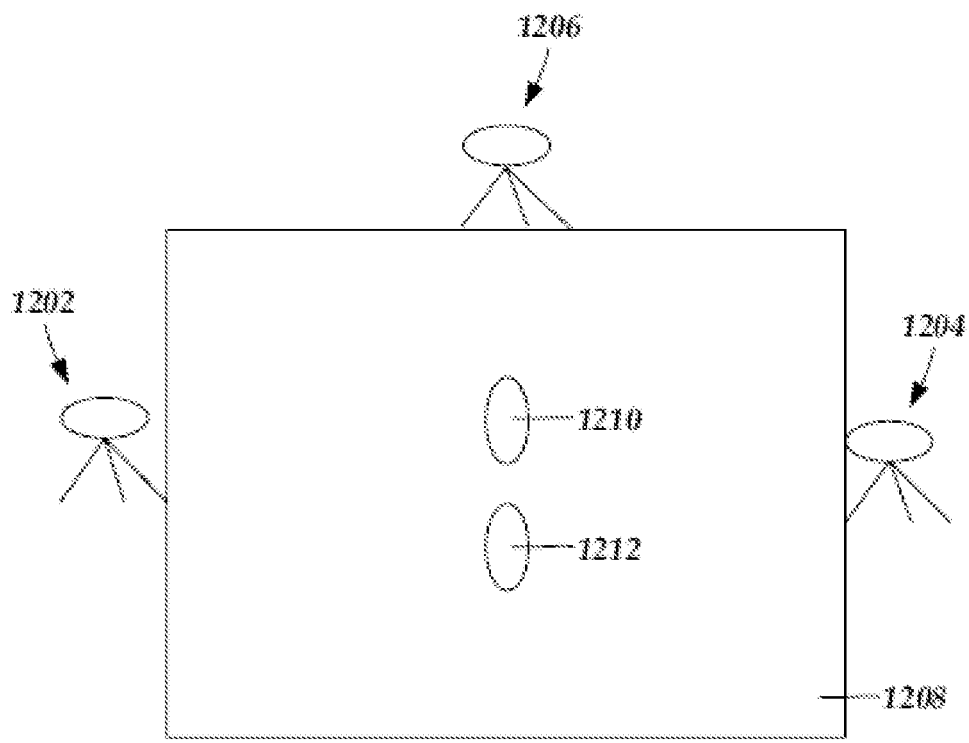
FIG. 12 is a schematic top view of one embodiment of an exemplary testing arrangement for capturing one or more static images or videos of a patient undergoing an ROM test or a dynamic sEMG test or both tests concurrently, according to the invention.

In at least some embodiments, further insight into the nature and extent of patient injury may be obtained by further including one or more video cameras, such as video camera 206, to capture one or more static images or, preferably, a video image of the performance of one or more of an ROM test and a dynamic sEMG test. FIG. 12 is a schematic top view of one embodiment of an exemplary testing arrangement for capturing one or more images or videos of a patient undergoing an ROM test and a dynamic sEMG test. In FIG. 12, three video cameras: 1202, 1204, and 1206, are placed around a mat 1208 that includes points 1210 and 1212 representing points for a patient to stand during performance of the ROM test and the dynamic sEMG test. In at least some embodiments, the video camera 1202 is positioned directly in front of a patient standing on points 1210 and 1212, while the video camera 1204 is positioned directly behind the patient, and while the video camera 1206 is positioned to one side of the patient.

In at least some embodiments, the addition of captured images or videos may be made available for review by one or more medical practitioners. In at least some embodiments, the data from one or more of the ROM test, dynamic sEMG test, and the videos (or static images) may be stored on the hub 104, one or more processors 202, or a storage device, and arranged so that one or more medical practitioners may use a slider to play back the patient's motion (for example, a forward flexion) and determine precisely the angle at which the patient has bent along with video of the patient's body showing the precise manner of movement. Moreover, similar testing may subsequently be performed on the same patient. Thus, comparison of two or more data sets may be performed to provide data for tracking patient progress over time.

Figure 13:
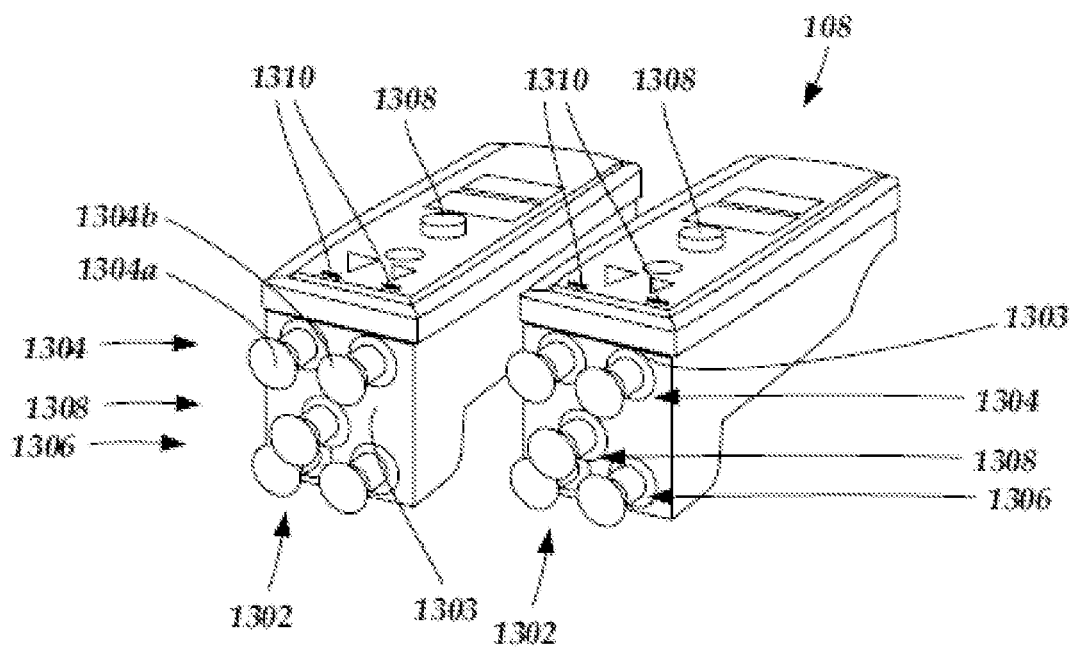
FIG. 13 is a schematic perspective view of one embodiment of a set of hand-held static sEMG scanners of the soft-tissue-injury diagnostic system shown in FIG. 1, according to the invention.

In at least some embodiments, the diagnostic system 100 includes scanners 108 for use by a user in administering a static sEMG test on a patient (measuring action potentials along selected muscle groups while the patient maintains a particular position). Sometimes a static sEMG test may involve a series of measurements taken during a set of successive placements of the scanners 108 against patient skin. FIG. 13 is a schematic perspective view of one embodiment of scanners 108 of the diagnostic system 100. The scanners 108 each include a plurality of measuring electrodes 1302 disposed on a front end 1303. In at least some embodiments, the measuring electrodes 1302 are arranged into sets, such as a first measuring electrode set 1304 and a second measuring electrode set 1306. The scanners 108 also include a ground 1308 disposed on the front end 1303.

In at least some embodiments, the scanners 108 are configured and arranged to be hand-held by a user during the performance of a static sEMG test. In at least some embodiments, the scanners 108 each include one or more controllers 1310 (e.g., buttons, switches, knobs, or the like). In at least some embodiments, a user of the scanners 108 may use the controllers 1310 to control progress during a static sEMG test without using a keypad, keyboard, or the like in between successive placements of the measuring electrodes 1304 against patient skin. In at least some embodiments, the scanner 108 includes one or more indicators 1312, such as one or more LEDs, which provide one or more indications to a user (e.g., battery level, on/off, connectivity, or the like) before, during, or after performance of a static sEMG test. In at least some embodiments, the scanners 108 include one or more gripping members (not shown) to facilitate gripping of the scanners 108 by the user 1602 while performing a static sEMG. For example, the scanners 108 may include one or more indentations configured and arranged to facilitate holding of the scanners 108 by the user 1602 during administration of a static sEMG test. In at least some embodiments, scanners 108 include a master power switch which, when in one position, maintain the scanners 108 powered off.

In at least some embodiments, the sets of measuring electrodes 1302 each include two electrodes, such as measuring electrodes 1304a and 1304b of the first measuring electrode set 1304. In at least some embodiments, the measuring electrodes within a set of measuring electrodes are horizontally spaced apart from one another on the front end 1303. In at least some embodiments, the sets of measuring electrodes are vertically spaced apart from one another. The ground 1308 can be disposed anywhere on the front end 108. In at least some embodiments, the ground 1308 is positioned vertically between the measuring electrode sets 1304 and 1306. In at least some embodiments, the ground 1308 is positioned horizontally between individual measuring electrodes within a set of measuring electrodes 1302.

In at least some embodiments, each set of measuring electrodes 1302 corresponds to a spinal level. Thus, the number of sets of measuring electrodes 1302 disposed on the scanner 108 may correspond to the number of spinal levels that can be simultaneously measured. In at least some embodiments, a user may place the measuring electrodes 1302 of the scanners 108 against a back of a patient in lateral proximity to the patient's spine at a desired level to measure action potentials. In at least some embodiments, the scanners 108 shown in FIG. 13 can be used to measure two spinal levels at a time for each placement of the scanners 108 against the patient, for example Cervical level 2 ("C2") and Cervical level 4 ("C4").

Any number of sets of measuring electrodes may be disposed on the scanner 108 including, for example, one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or more sets of measuring electrodes. It will be understood that additional sets of measuring electrodes may be disposed on the scanner 108, as well.

In a least some embodiments, the scanners 108 communicate with the hub 104 (and, optionally, one or more processors 202, via the hub 104). In at least some embodiments, the scanners 108 are wireless. When the scanners 108 are wireless, a user and patient are not limited to either being positioned in the immediate vicinity of the hub 104 or creating a potential hazard by extending one or more conductors over a space where the conductors may present a hazard, such as potentially being tripped over. Consequently, wireless scanners 108 may be used, for example, at a screening (where a user is at a mall, health fair, car show, or the like) to go out into a crowd to test people without needing to entice people into a testing center. In at least some embodiments, the results of a static sEMG test may be shown in real-time on one or more visual displays 204. In at least some embodiments, data from a static sEMG may be transmitted at least thirty feet to the hub 104.

In at least some embodiments, the diagnostic system 100 may include multiple sets of scanners 108 so that multiple static sEMG tests may be performed on multiple patients while the data from each static sEMG test are input to the hub 104 (and, optionally, to one or more processors 202), processed, and the results output to one or more displays, such as the visual display 204. In at least some embodiments, the results of multiple static sEMG tests may be displayed concurrently on a single visual display 204. For example, the visual display 204 may include a split screen with static sEMG test results for two or more patients.

The measuring electrodes 1302 may be formed from many different conductive materials suitable for placement against the skin of a patient including, for example, gold, stainless steel, silver, silver chloride, and the like or combinations thereof. The ground 1308 may also be formed from many different conductive materials suitable for placement against the skin of a patient including, for example, gold, stainless steel, silver, silver chloride, and the like or combinations thereof. In at least some embodiments, the ground 1308 is formed from the same conductive material as the measuring electrodes 1302.

In at least some embodiments, the grounds 1308 of the scanners 108 are retractable in order to promote an improved contact between each ground 1308 and a patient when the scanners 108 are placed against the patient, and to also promote improved contact between the sets of measuring electrodes 1304 and 1306 and the patient, especially when the sets of measuring electrodes 1304 and 1306 are contacting curved portions of the patient, such as a patient's back.

Figure 14A:
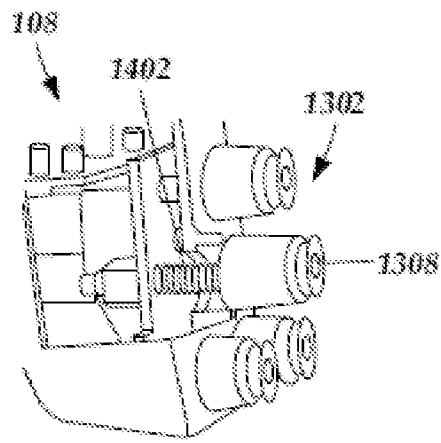
FIG. 14A is a schematic perspective view of one embodiment of one of the static sEMG scanners of FIG. 13 with a ground in an extended position and a portion of an outer casing of the static sEMG scanner removed, according to the invention.
Figure 14B:
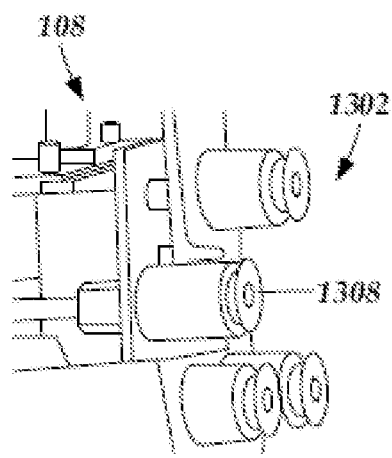
FIG. 14B is a schematic perspective view of one embodiment of one of the static sEMG scanners shown in FIG. 13 with a ground in a refracted position and a portion of an outer casing of the static sEMG scanner removed, according to the invention.

FIG. 14A is a schematic perspective view of one embodiment of one of the scanners 108 with the ground 1308 in an extended position and a portion of an outer casing of the scanner 108 removed, for clarity of illustration. In at least some embodiments, a spring, such as spring 1402, is positioned within the scanner 108 and used to provide the retractability of the ground 1308. It will be understood that any suitable type of spring may be implemented in the scanners 108 to provide retractability of the ground 1308 (e.g., tension, compression, torsional, coiled, flat, leaf, cantilever, hairspring, V-spring, or the like or combinations thereof). In at least some embodiments, by allowing the ground 1308 to retract, the scanner 108 may be better able to adjust to contours of the body, and allow the first and second sets 1304 and 1306, respectively, of the measuring electrodes 1302 to contact the skin of a patient, even when there is a curve in the patient's body which, without retractability would cause the ground 1308 to lift at least one of the sets 1304 and 1306, respectively, of the measuring electrodes 1302 off the skin of the patient. FIG. 14B is a schematic perspective view of one embodiment of one of the scanners 108 with the ground 1308 in a retracted position and a portion of an outer casing of the scanner 108 removed, for clarity of illustration.

In at least some embodiments, action potentials measured by the scanners 108 may be no greater than one milli-volt. Accordingly, ground loop protection and noise reduction may be important concerns. In at least some embodiments, noise is reduced, in part, by using wire links for each measuring electrode that are of similar length.

Figure 15:
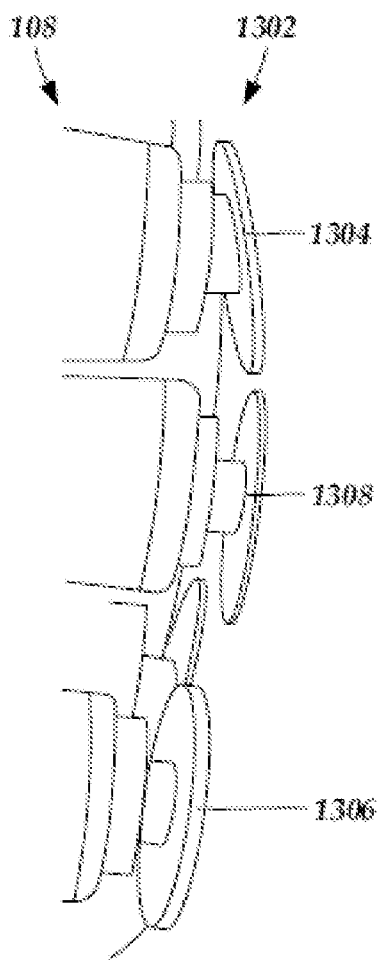
FIG. 15 is a schematic side view of one embodiment of one of the static sEMG scanners shown in FIG. 13 positioned against a patient such that the measuring electrodes are individually pivoted according patient contours, according to the invention.

In at least some embodiments, one or more of the measuring electrodes 1302 are pivotable to adapt to changes in body contours of a patient when, for example, the scanner 108 is pressed against the patient's body. FIG. 15 is a schematic side view of one embodiment of the measuring electrodes 1302 of one of the scanners 108 with the measuring electrodes 1304 and 1306 each pivoted at different angles from one another. In at least some embodiments, one or more of the measuring electrodes 1302 utilize an independent suspension system. In at least some embodiments, one or more of the measuring electrodes 1302 utilize a ball-and-socket system.

Figure 16:
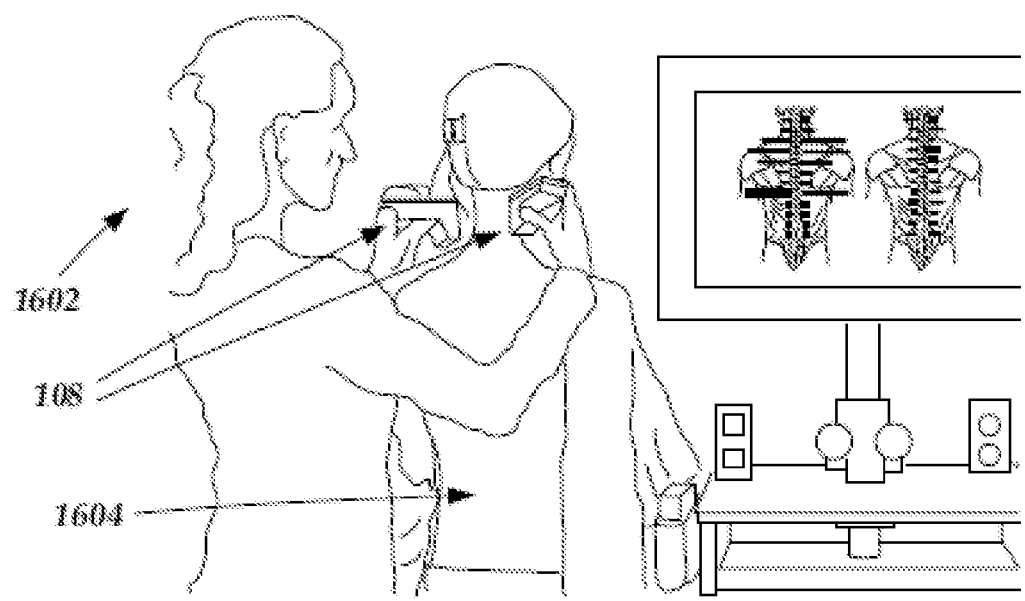
FIG. 16 is a schematic view of one embodiment of the static sEMG scanners shown in FIG. 13 being used by a user to perform a static sEMG test on a patient, according to the invention.

FIG. 16 is a schematic view of one embodiment of a user 1602 using the scanners 108 to perform a static sEMG test on a patient 1604. In at least some embodiments, each of the scanners 108 is positioned in lateral proximity to a spine of the patient 1604 at various levels of the spine. For example, in FIG. 16 the scanners 108 are positioned in lateral proximity to a cervical portion of the patient's spine. As discussed above, the scanners 108 each include two sets of measuring electrodes 1302. Thus, in FIG. 16 measurements can be taken concurrently at two spinal levels during each placement of the scanners 108 against the patient.

Over time, a series of measurements are obtained at different levels of the patient's spine. Action potentials of muscles are measured and the corresponding data is transferred to the hub 104 (and, optionally, one or more processors 202 via the hub 102), the data is processed, and results are displayed on one or more displays, such as the one or more visual displays 204.

In at least some embodiments, the scanners 108 are powered by one or more batteries. In at least some embodiments, during a static sEMG test the corresponding software executes a command to power off the scanners 108 for a period of time between successive placements to save battery power. In at least some embodiments, during a static sEMG test the corresponding software executes a command to power on the scanners 108 when the scanners 108 are positioned against a patient, or when the controller 1301 is engaged. In at least some embodiments, during a static sEMG test the corresponding software executes a command to power off the scanners 108 after the one or more controllers 1308 are engaged.

In at least some embodiments, the hub 104 or the one or more processors 202 provide a prompt to alert the user 1602 when the scanners 108 are properly positioned against the patient 1604. In some embodiments, one or more of the positioning information and instructions for progressing through a static sEMG test is displayed on the one more visual displays 204. In other embodiments, the positioning information is provided via one or more voice commands.

Figure 17:
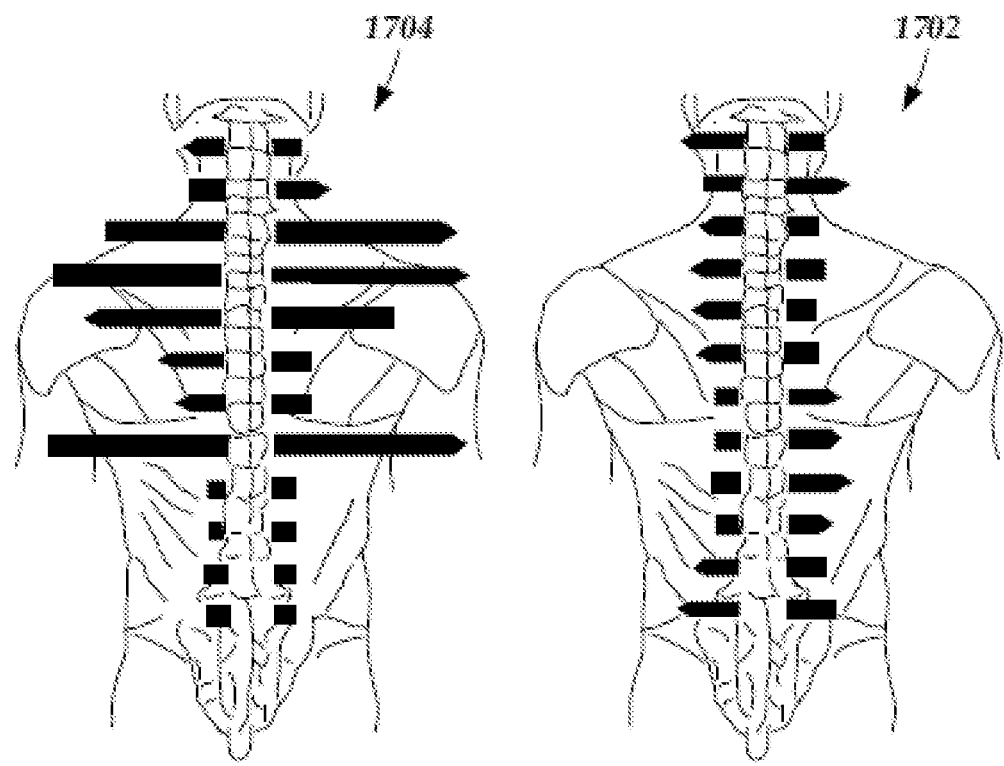
FIG. 17 is a schematic view of one embodiment of two exemplary results from a static sEMG test performed on a patient, according to the invention.

FIG. 17 is a schematic view of one embodiment of two exemplary results 1702 and 1704 for a static sEMG test performed on a patient. In at least some embodiments, the two results 1702 and 1704 are from a single patient. In at least some embodiments, the two results 1702 and 1704 are from two different patients. In at least some embodiments, one of the two results 1702 and 1704 is from a patient and the other result is a model result, such as an "ideal" result to compare against the patient's result.

As discussed above, the scanners 108 may include various numbers of sets of measuring electrodes. In at least some embodiments, more than two sets of measuring electrodes may be used. Additionally, in at least some embodiments additional grounds may also be used. In some embodiments, the measuring electrodes are coupled to hand-held scanners, such as the scanners 108. In at least some embodiments, measuring electrodes are coupled to scanners that may be self-standing or mounted to one or more planar surfaces, such as a wall.

Figure 18:
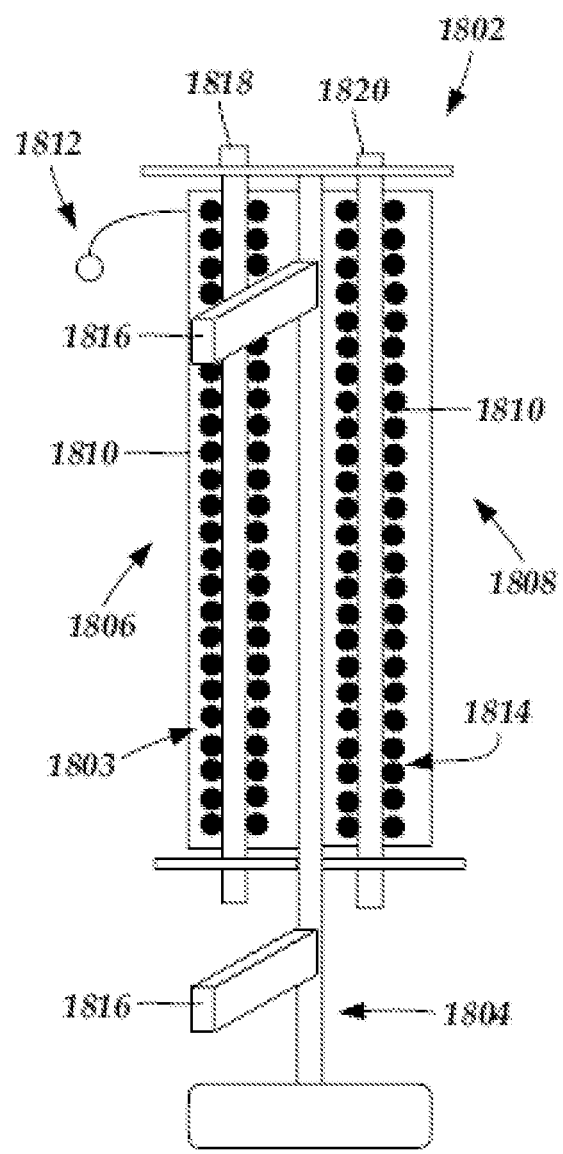
FIG. 18 is a schematic perspective view of one embodiment of a mountable static sEMG scanner of the soft-tissue-injury diagnostic system shown in FIG. 1, according to the invention.

FIG. 18 is a schematic perspective view of one embodiment of a static sEMG scanner 1802 with twenty-four sets of measuring electrodes 1803. The static sEMG scanner 1802 includes a base 1804, two columns 1806 and 1808 of sets of measuring electrodes 1803 mounted to one or more mounting boards 1810, and at least one ground 1812. Each column 1806 and 1808 includes a plurality of sets of measuring electrodes 1803, such as set 1814. In at least some embodiments, the static sEMG scanner 1802 is coupled to the hub 104.

In at least some embodiments, the measuring electrodes 1803 are retractable. Thus, in at least some embodiments when a patient contacts the measuring electrodes 1803, the measuring electrodes 1803 retract some amount of distance. In at least some embodiments, when the static sEMG scanner 1802 is mounted to a wall, the static sEMG scanner 1802 is positioned away from the wall far enough to accommodate the retraction of the measuring electrodes 1803 as the patient contacts the measuring electrodes 1803. In at least some embodiments, the static sEMG scanner 1802 includes one or more spacer bars 1816 to prevent one or more of the measuring electrodes 1803 from contacting a wall on which the static sEMG scanner 1802 is mounted when a patient is contacting (and consequently retracting) one or more of the measuring electrodes 1803. In at least some embodiments, the measuring electrodes 1803 may be adjusted for improved contact against patient skin during a static sEMG test. In at least some embodiments, the two columns 1806 and 1808 of measuring electrodes 1803 are moveably mounted such that they can be moved horizontally closer together or further apart from one another to improve measuring electrode 1803 contact with patients with spines of various widths. In at least some embodiments, the height from the floor of each of the columns 1806 and 1808 may be raised or lowered to improve measuring electrode 1803 contact with patients of different heights.

In at least some embodiments, a pivot extends between measuring electrodes 1803 of each set of measuring electrodes 1803 to improve contact with patients. In FIG. 18, the pivots are shown as two bars 1818 and 1820 extending vertically between measuring electrodes of each set of measuring electrodes 1803. In at least some embodiments, the measuring electrodes 1803 are mounted on a pliable substance, such as rubber, which facilitates a left/right pivot for each set of measuring electrodes 1803.

In at least some embodiments, accompanying software distinguishes measuring electrodes 1803 making contact with patient skin from measuring electrodes 1803 not making patient-skin contact. In at least some embodiments, the software can detect when action potential measurements from one or more of the measuring electrodes 1803 are zero (no patient contact). In at least some embodiments, a user can select the top and bottom measuring electrodes 1803 of the two columns 1806 and 1808 making contact with a patient from a display showing the measuring electrodes 1803. For example, the user can select that the top two sets of measuring electrodes 1803 of each of the mounting boards 1810 are to be ignored (e.g., when performing a static sEMG test on a particularly short patient). As another example, the user may select the top measuring electrode sets to be at the Cervical level 4 ("C4") of a patient and the bottom measuring electrode sets to be at Lumbar level 1 ("L1") of the patient, with the bottom six sets of measuring electrodes not contacting the patient.

Figure 19:
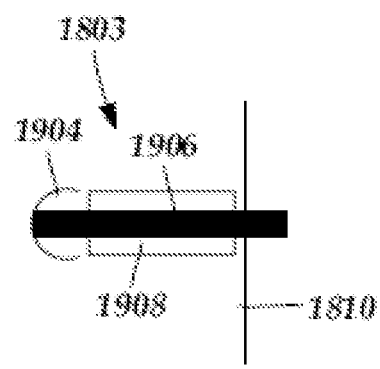
FIG. 19 is a schematic side view of one embodiment of a measuring electrode of the static sEMG scanner shown in FIG. 18, according to the invention.

FIG. 19 is a schematic side view of one embodiment of one of the measuring electrodes 1803 of the static sEMG scanner 1802. The measuring electrode 1803 includes a curved contact surface 1904 mounted to a conductive member 1906 which, in turn is mounted to the mounting board 1810. In at least some embodiments, the conductive member 1906 is coupled to a spring 1908. In at least some embodiments, the spring 1908 facilitates the retraction of the measuring electrode 1803 when a patient contacts the contact surface 1904 of the measuring electrode 1803. In one specific embodiment, the spring 1908 is configured and arranged so that the measuring electrode 1803 may be retracted up to twelve inches (approximately 30 cm).

Figure 20:
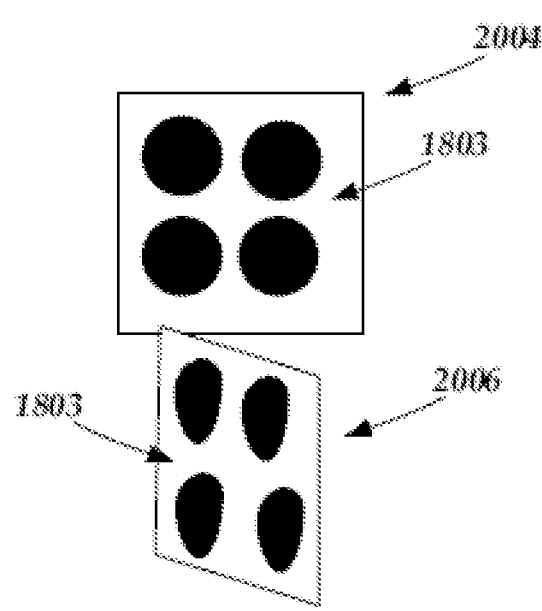
FIG. 20 is a schematic view of one embodiment of a set of four measuring electrodes of the static sEMG scanner shown in FIG. 18 in two positions, the second position horizontally pivoted from the first position, according to the invention.

FIG. 20 is a schematic view of one embodiment of four measuring electrodes 1803 in a first position 2004 and a second position 2006 that is horizontally pivoted from the first position 2004. In at least some embodiments, pivotable measuring electrodes may improve contact between the measuring electrodes 1803 and a patient when the patient is contacting the measuring electrodes 1803. In at least some embodiment, the measuring electrodes 1803 are pivoted about a pivot, such as one of the bars 1818 and 1820. In some embodiments, the measuring electrodes 1803 may pivot horizontally. In other embodiments, the measuring electrodes 1803 may pivot vertically. In other embodiments, the measuring electrodes 1803 may pivot along other axes other than a horizontal or a vertical axis. In other embodiments, patient contact is improved by using a pliable material, such as rubber, to form the non-contact surface of the measuring electrodes, the pliable material facilitating the bending of the measuring electrodes as needed when a patient is contacting the contact surface 1904 so as to improve contact.

Figure 21:
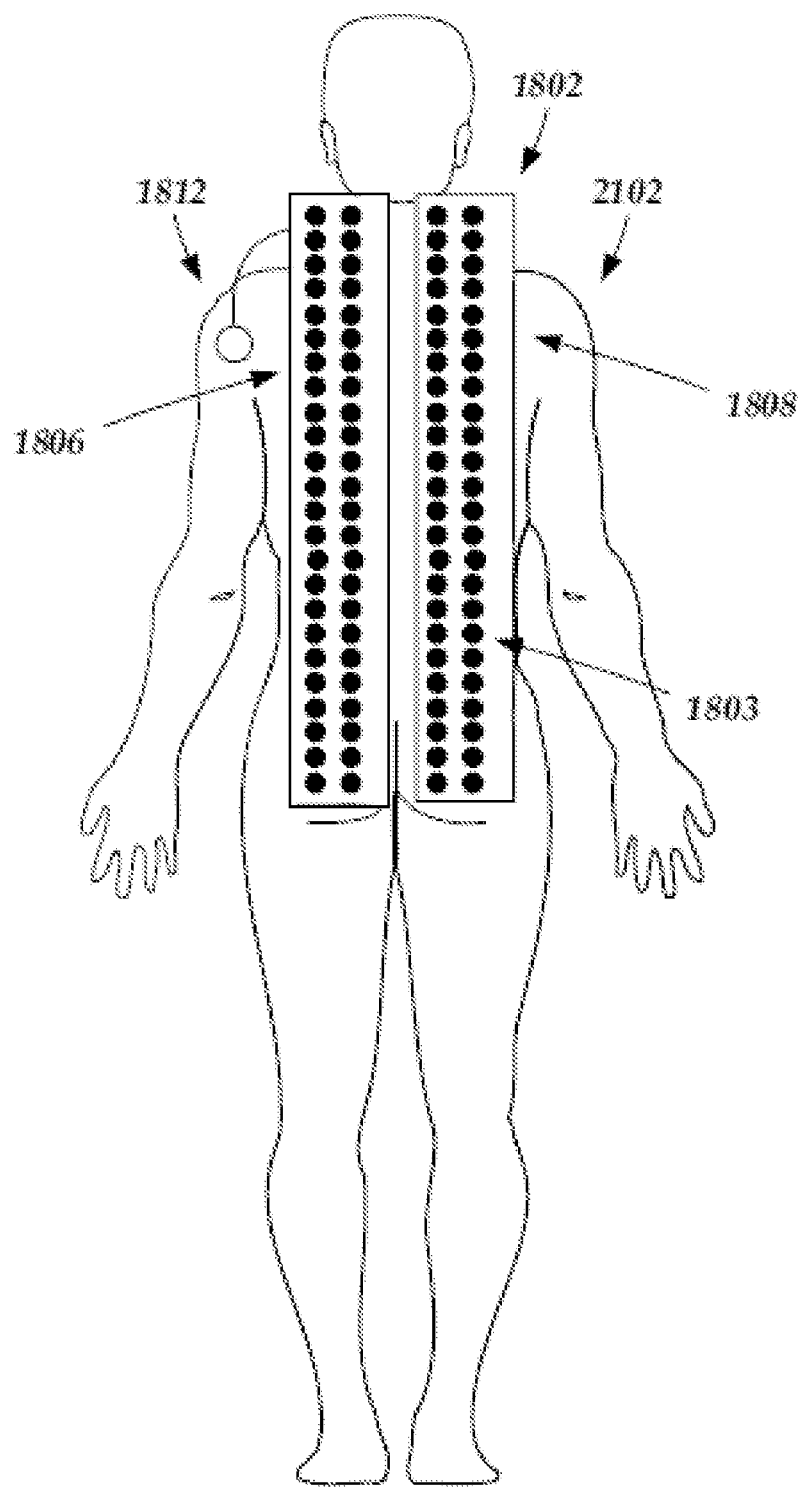
FIG. 21 is a schematic rear view of one embodiment of the static sEMG scanner shown in FIG. 18 aligned against a back of a human figure, according to the invention.

FIG. 21 is a schematic rear view of one embodiment of the static sEMG scanner 1802 aligned against a back of a human FIG. 2102. In FIG. 21 the two columns 1806 and 8108 of the measuring electrodes 1803 and the ground 1812 are contacting the back of the human FIG. 2102. In at least some embodiments, the two columns 1806 and 1808 of the measuring electrodes 803 are configured and arranged so that the measuring electrodes 1803 are contacting the back of the human FIG. 2102 in lateral proximity to the spine of the human FIG. 2102.

Figure 22:
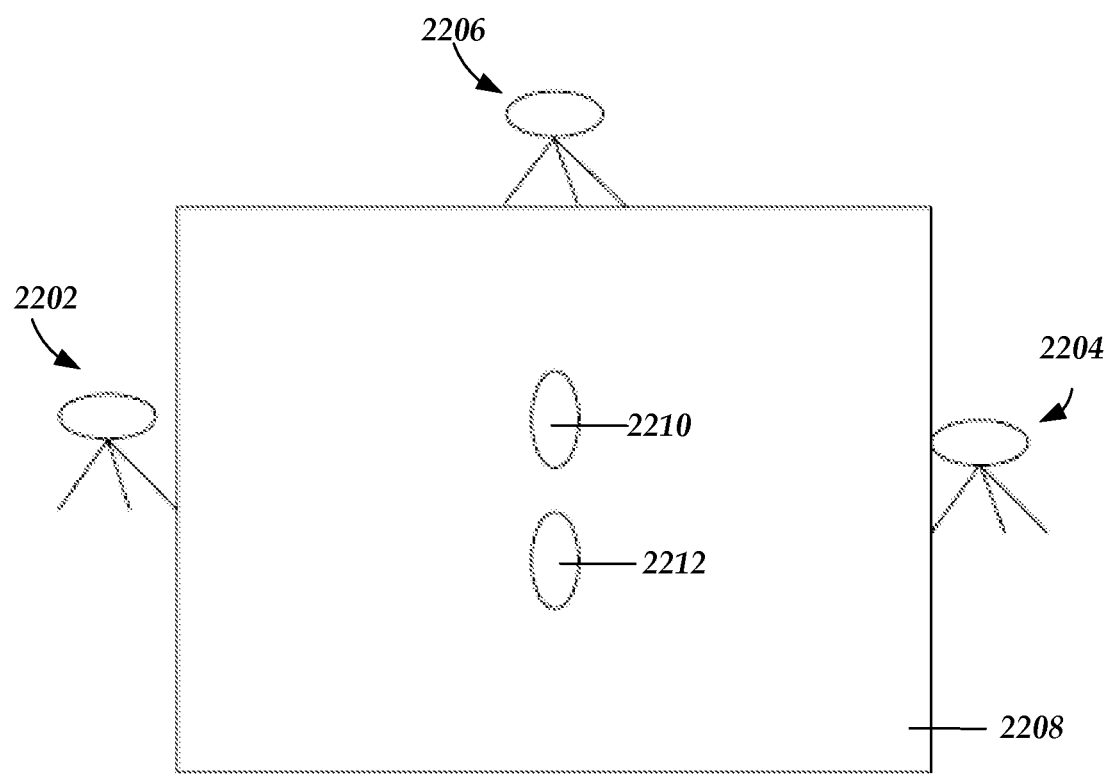
FIG. 22 is a schematic top view of one embodiment of an exemplary testing arrangement for capturing one or more images or videos of a patient while undergoing a static sEMG test.

In at least some embodiments, further insight into the nature and extent of patient injury may be obtained by further including one or more video cameras, such as video camera 206, to capture one or more images or videos of the performance of the static sEMG test. FIG. 22 is a schematic top view of one embodiment of an exemplary testing arrangement for generating images of the patient undergoing a static sEMG test. In FIG. 22, three video cameras: 2202, 2204, and 2206, are positioned around a mat 2208 that includes regions 2210 and 2212, representing a location for a patient to stand on during performance of the static sEMG test. In at least some embodiments, the video camera 2202 is positioned directly in front of a patient standing on the regions 2210 and 2212, while the video camera 2204 is positioned directly behind the patient, and while the video camera 2206 is positioned to one side of the patient. In at least some embodiments, at least one of one or more videos or one or more still images may be generated of the patient while the patient undergoes a static sEMG test.

In at least some embodiments, the addition of video (or one or more captured images) from one or more different angles may be made available for review by one or more medical practitioners. In at least some embodiments, the data from the static sEMG test and the one or more captured video (or static images) may be stored on the one or more processors 202 so that one or more medical practitioners may see precisely the positioning of the patient when the data was collected for a static sEMG test. Moreover, a similar test may be subsequently performed on the same patient in order to track patient progress over time.

As discussed above, the images obtained from the above diagnostic system may be embedded with various contact messages. Because the medical images are modified or otherwise configured to not include private patient information, the images with the embedded messages may be electronically sent to a patient for sharing with others. The following discloses environments and operational aspects of embodiments that are usable for embedding and sending to patient's medical images personalized with contact messages that may be subsequently shared by the patient with others.

Figure 23:
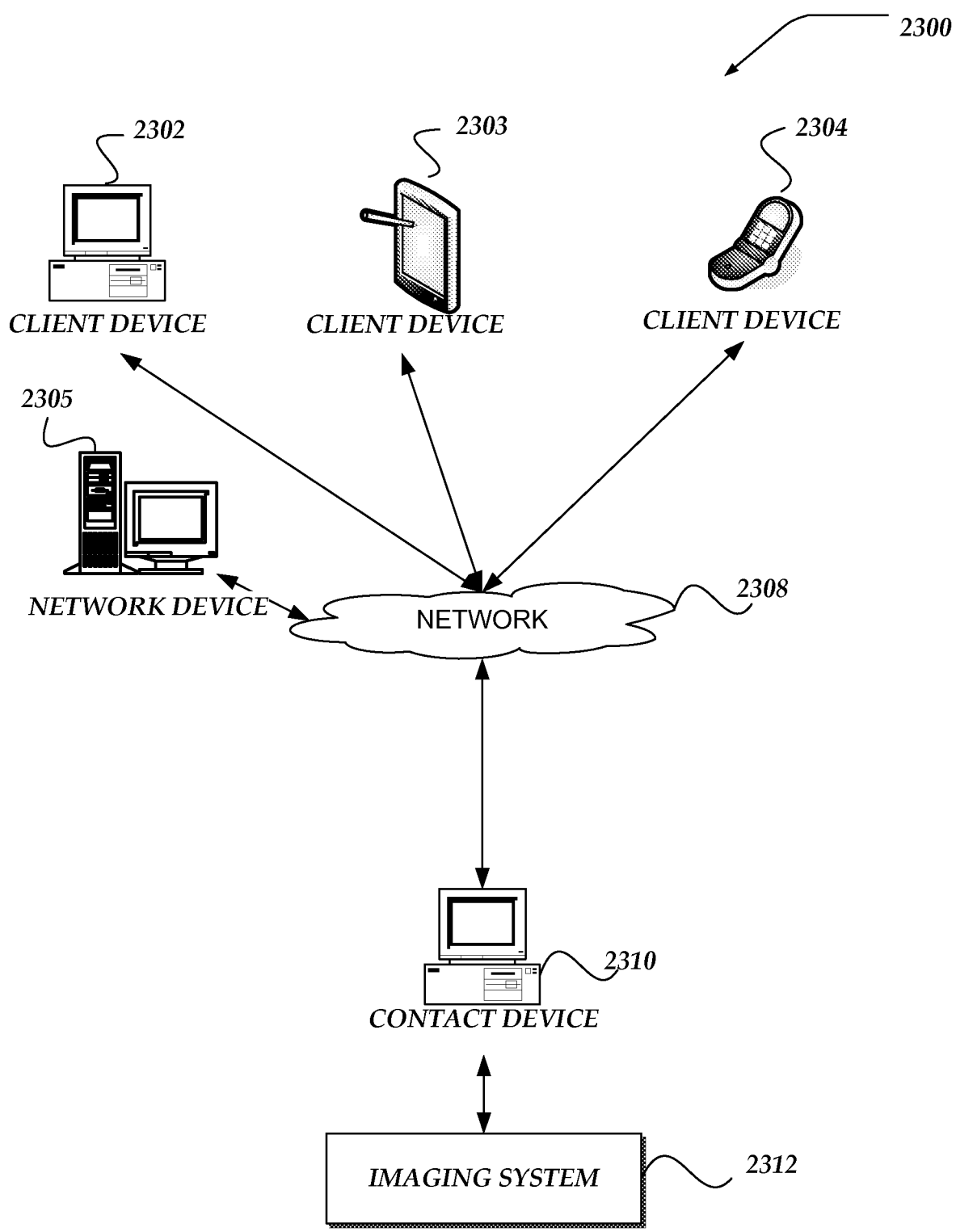
FIG. 23 shows various components of one embodiment of an illustrative environment in which the described embodiments may be practiced.

FIG. 23 shows various components of an illustrative environment 2300 in which the described embodiments for embedding images with contact messages may be practiced. Not all the components may be required to practice the described embodiments, and variations in the arrangement and type of the components may be made without departing from the spirit or scope of the described embodiments. However, as shown FIG. 23 illustrates client devices 2302-2304, network 2308, network device 2305, contact device 2310, and imaging system 2312.

Generally, client devices 2302-2304 may include virtually any computing device capable of receiving and sending a message over a network, such as network 2308, to and from another computing device, such as content device 2310, network device 2305, each other, and the like. The set of such devices may include devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, client devices 2302-2304 may be any device that is capable of connecting using a wired or wireless communication medium such as a personal digital assistant (PDA), pocket PC, wearable computer, and any other device that is equipped to communicate over a wired and/or wireless communication medium. The set of such devices may also include devices that typically connect using a wired communications medium such as personal computers, multiprocessor systems, microprocessor-based or programmable consumer electronics, network PCs, and the like.

Each client device within client devices 2302-2304 may include a browser application that is configured to send, receive, and display web pages, and the like. The browser application may be configured to receive and display graphics, text, multimedia, and the like, employing virtually any web based language, including, but not limited to Standard Generalized Markup Language (SMGL), such as HyperText Markup Language (HTML), extensible markup language (XML), a Handheld Device Markup Language (HDML), such as Wireless Markup Language (WML), WMLScript, JavaScript, and the like. Client devices 2302-2304 may further include a messaging application configured to send and/or receive a message to/from another computing device employing another mechanism, including, but not limited to instant messaging (IM), email, Short Message Service (SMS), Multimedia Message Service (MMS), internet relay chat (IRC), mIRC, Jabber, and the like. Moreover, client devices 2302-2304 are configured to enable a user to access a social networking site, such as Facebook sites, Flicker sites, or the like, to access and/or post various content. For example, a user of a client device may receive from network device 2305 and/or contact device 2310 a medical diagnostic image that is embedded with one or more contact messages that the user may then elect to post on a social networking site, and/or otherwise share with others.

Network 2308 is configured to couple network enabled devices, such as client devices 2302-2304, contact device 2310, and network device 2305, with other network enabled devices. Network 2308 is enabled to employ any form of computer readable media for communicating information from one electronic device to another. In one embodiment, network 2308 may include the Internet, and may include local area networks (LANs), wide area networks (WANs), direct connections, such as through a universal serial bus (USB) port, other forms of computer-readable media, or any combination thereof. On an interconnected set of LANs, including those based on differing architectures and protocols, a router may act as a link between LANs to enable messages to be sent from one to another. Also, communication links within LANs typically include fiber optics, twisted wire pair, or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art.

Network 2308 may further employ a plurality of wireless access technologies including, but not limited to, 2nd (2G), 3rd (3G), 4th (4G) generation radio access for cellular systems, Wireless-LAN, Wireless Router (WR) mesh, and the like. Access technologies such as 2G, 3G, 4G, and future access networks may enable wide area coverage for network devices, such as client devices 2302-2304, or the like, with various degrees of mobility. For example, network 2308 may enable a radio connection through a radio network access such as Global System for Mobil communication (GSM), General Packet Radio Services (GPRS), Enhanced Data GSM Environment (EDGE), Wideband Code Division Multiple Access (WCDMA), and the like.

Furthermore, remote computers and other related electronic devices could be remotely connected to either LANs or WANs via a modem and temporary telephone link, a DSL modem, a cable modem, a fiber optic modem, an 802.11 (Wi-Fi) receiver, and the like. In essence, network 2308 includes any communication method by which information may travel between one network device and another network device.

Network device 2305 may include any computing device capable of communicating content to or from another computing device, such as client devices 2302-2304, and/or contact device 2310. In one embodiment, network device 2305 might represent a computing device used within a business, such as a medical business, or the like. In some embodiments, network device 2305 might operate to manage a database, spreadsheet, or the like. In some embodiments, network device 2305 might receive patient information, including an email address, or other contact information, usable to send a patient a message. In some embodiments, such patient information might be manually entered into network device 2305, or received over network 2308 from a client device, or contact device 2310. In some embodiments, network device 2305 might receive information from contact device 2310 that may be used to schedule follow-up sessions with a patient, and/or to send other information to a patient.

Although network device 2305 is shown as a single computing device, in other embodiments, network device 2305 might represent a plurality of distinct network devices. Devices that may operate as network device 2305 includes personal computers, desktop computers, multiprocessor systems, microprocessor-based or programmable consumer electronics, network PCs, server devices, and the like.

One embodiment of contact device 2310 is discussed in more detail below in conjunction with FIG. 24. Briefly, however, contact device 2310 may include virtually any computing device that may be configured to embed contact messages into a digital image and send the modified image over the network. Thus, contact device 2310 might represent an embodiment of the one or more processors 202 and one or more visual displays 204 discussed above in conjunction with FIG. 2. Therefore, in some embodiments, contact device 2310 might be included within imaging system 2312. In other embodiments, contact device 2310 might operate separate from imaging system 2312. In some embodiments, contact device 2310 might be directly coupled to imaging system 2312 through hub 104. In other embodiments, contact device 2310 might be coupled to imaging system 2312 through a cellular network modem or card, or other mechanism, including through a network such as network 2308, a local area network (LAN), or any of a variety of other networking mechanisms. In any event, in some embodiments, contact device 2310 may be configured to perform actions as discussed further below in conjunction with FIG. 25.

As noted, environment 2300 includes imaging system 2312, which may represent one or more of the medical diagnostic instrumentation systems discussed above. However, imaging system 2312 is not constrained to the above imaging systems, and others may also be used. Moreover, imaging system 2312 might even represent non-medical imaging systems.

Figure 24:
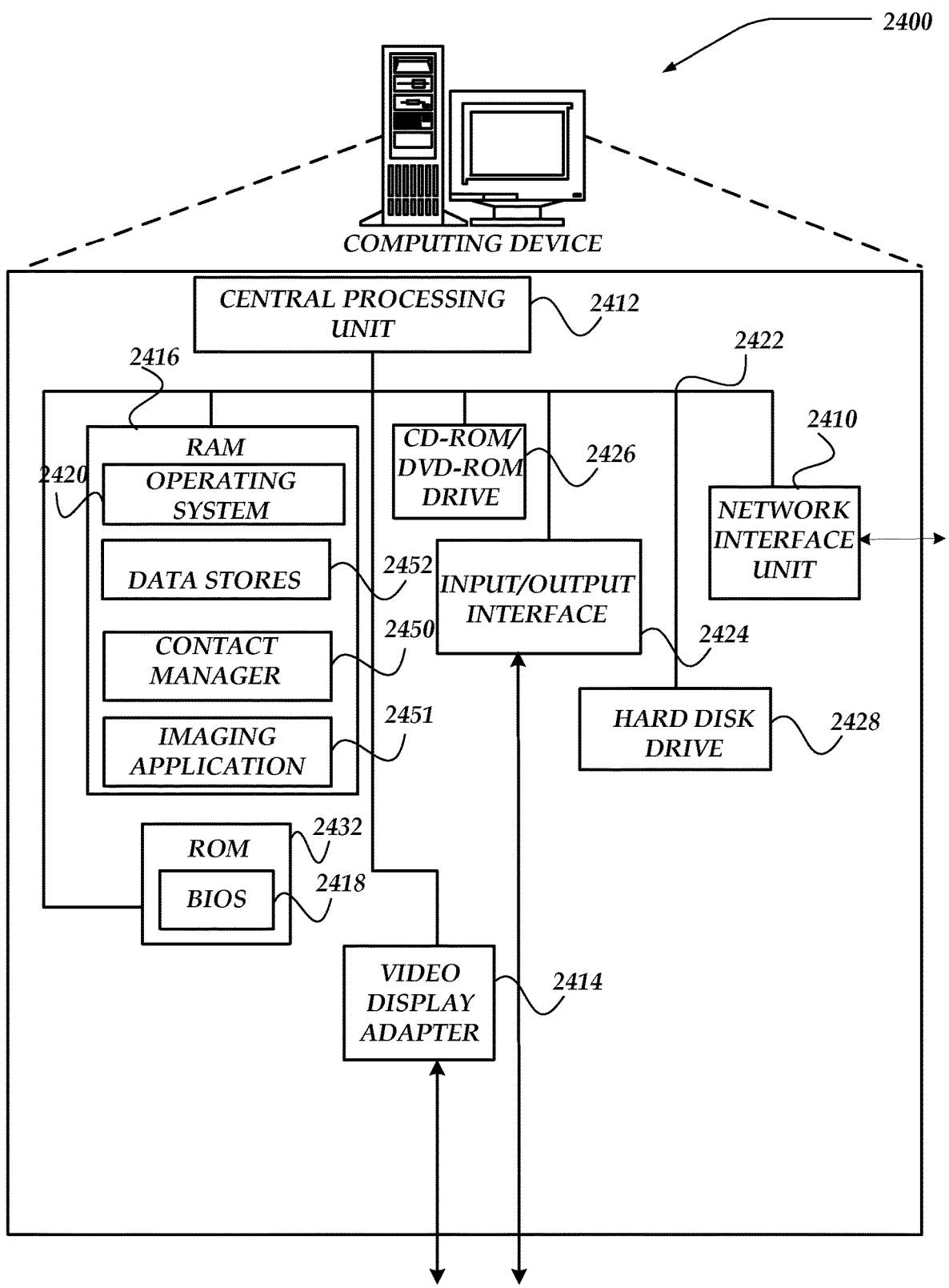
FIG. 24 illustrates on embodiment of a computing device usable to generate and transmit one or more contact messages embedded within a medical diagnostic image, or other images.

FIG. 24 illustrates on embodiment of a computing device usable to generate and transmit contact messages embedded within personalized medical images or other images, such as discussed above in conjunction with FIG. 23.

Computing device 2400 may include many more components than those shown. The components shown, however, are sufficient to disclose an illustrative embodiment for practicing the embodiments. Computing device 2400 may represent, for example, contact device 2310 of FIG. 23.

Computing device 2400 includes one or more central processing unit 2412, video display adapter 2414, and a mass memory, all in communication with each other via bus 2422. The mass memory generally includes RAM 2416, ROM 2432, and one or more permanent (non-transitory) mass storage devices, such as hard disk drive 2428, tape drive, CD-ROM/DVD-ROM drive 2426, and/or floppy disk drive. The mass memory stores operating system 2420 for controlling the operation of server device 2400. BIOS 2418 is also provided for controlling the low-level operation of computing device 2400. As illustrated in FIG. 24, computing device 2400 also can communicate with the Internet, or some other communications network, such as network 2308 of FIG. 23, via network interface unit 2410, which is constructed for use with various communication protocols including the TCP/IP protocol. Network interface unit 2410 is sometimes known as a transceiver, transceiving device, or network interface card (NIC).

Computing device 2400 may also include input/output interface 2424 for communicating with external devices, such as a mouse, keyboard, scanner, or other input devices not shown in FIG. 24.

The mass memory as described above illustrates another type of non-transitory computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices, or any other non-transitory medium which can be used to store the desired information and which can be accessed by a computing device.

Memory further includes one or more data stores 2452, which can be utilized to store, among other things, application programs and/or other data. The application programs may include computer executable instructions which, when executed by computing device 2400 perform a variety of actions. Accordingly, programs may include a browser program of computer executable instructions, which may be run under control of operating system 2420 to enable and manage various actions, including those discussed below in conjunction with FIG. 25. Other examples of application programs include calendars, contact managers, task managers, transcoders, database programs, word processing programs, spreadsheet programs, games, and so forth. The mass memory may include imaging application 2451 that is configured to perform operations as discussed above in conjunction with FIGS. 1-22. The mass memory may also include contact manager 2450.

Contact manager 2450 may be installed onto computing device 2400 using any of a variety of mechanisms, including over a network, via a portable non-transitory computer-readable storage device, or the like. Once installed, contact manager 2450 may be configured to receive various information usable for generating and embedding contact messages into a digital image, such as a medial diagnostic image, that may then be sent over a network to another computing device. Moreover, contact manager 2450 may be readily updated, and configured to enable contact message information to be revised and stored for use with a plurality of contact messages, or a single contact message.

Contact manager 2450 is configured to receive patient information, including, for example, an email address, or other address for which electronic messages may be sent. In one embodiment, contact manager 2450 may store the received patient information securely within data stores 2452. In some embodiments, at least a portion of the patient information might be sent over a network in a secure manner, to another network device.

Contact manager 2450 may further receive a digital image from another device, or even from imaging application 2451. Contact manager 2450 may then use any of a variety of techniques to embed one or more contact messages into a digital image, such that the embedded messages are visible by a recipient. Without limit, embedding of the one or more contact messages include layering and/or weaving of the one or more contact messages into the digital image; using watermark techniques to visibly embed the one or more contact messages into the digital image; or any of a variety of other techniques. As used herein, watermarking refers to manipulating the digital image so as to modify the digital image in a manner directed towards making removal of the one or more contact messages resistant to tampering. Moreover, contact manager 2450 may be used to select a number contact messages to embed into the digital image, as well as location(s) within the digital image in which to place the one or more contact messages. One non-limiting, non-exhaustive example of a medical diagnostic image having embedded contact messages is described in more detail below in conjunction with FIG. 26.

Contact manager 2450 may further be used to obfuscate or otherwise delete information within the digital image that might be sensitive, include patient private information, or the like. In one embodiment, such information might be deleted using a pixel by pixel replacement technique; however, other techniques might also be used to modifying the digital image data that represents the medical diagnostic image.

Contact manager 2450 is then configured to electronically transmit the modified digital image having the one or more embedded contact messages over a network to a computing device, such as client devices 2302-2304 of FIG. 23 to enable a patient to, among other actions, share the modified digital image with others, or post the modified digital image on a social networking site. As discussed below, in some embodiments, one or more of the embedded contact messages may include a hyperlink, or other mechanism, that allows the patient to select and access other information. For example, the link or other mechanism might allow the patient to contact a medical professional to schedule a follow-up session; to access a website to obtain additional information about the digital image, the medical professional, or the like. Contact manager 2450 may further send patient information, and/or the modified digital image to the professional's network device for storage, and/or scheduling additional marketing, or follow-up actions. For example, contact manager 2450 may store a date of when a test was performed, and automatically send out a reminder message, optionally with a patient's most current test graphic image with an embedded message such as "time to schedule a re-exam," or the like.

Contact manager 2450 may employ a process such as described below in conjunction with FIG. 25 to perform at least some of its actions.

Figure 25:
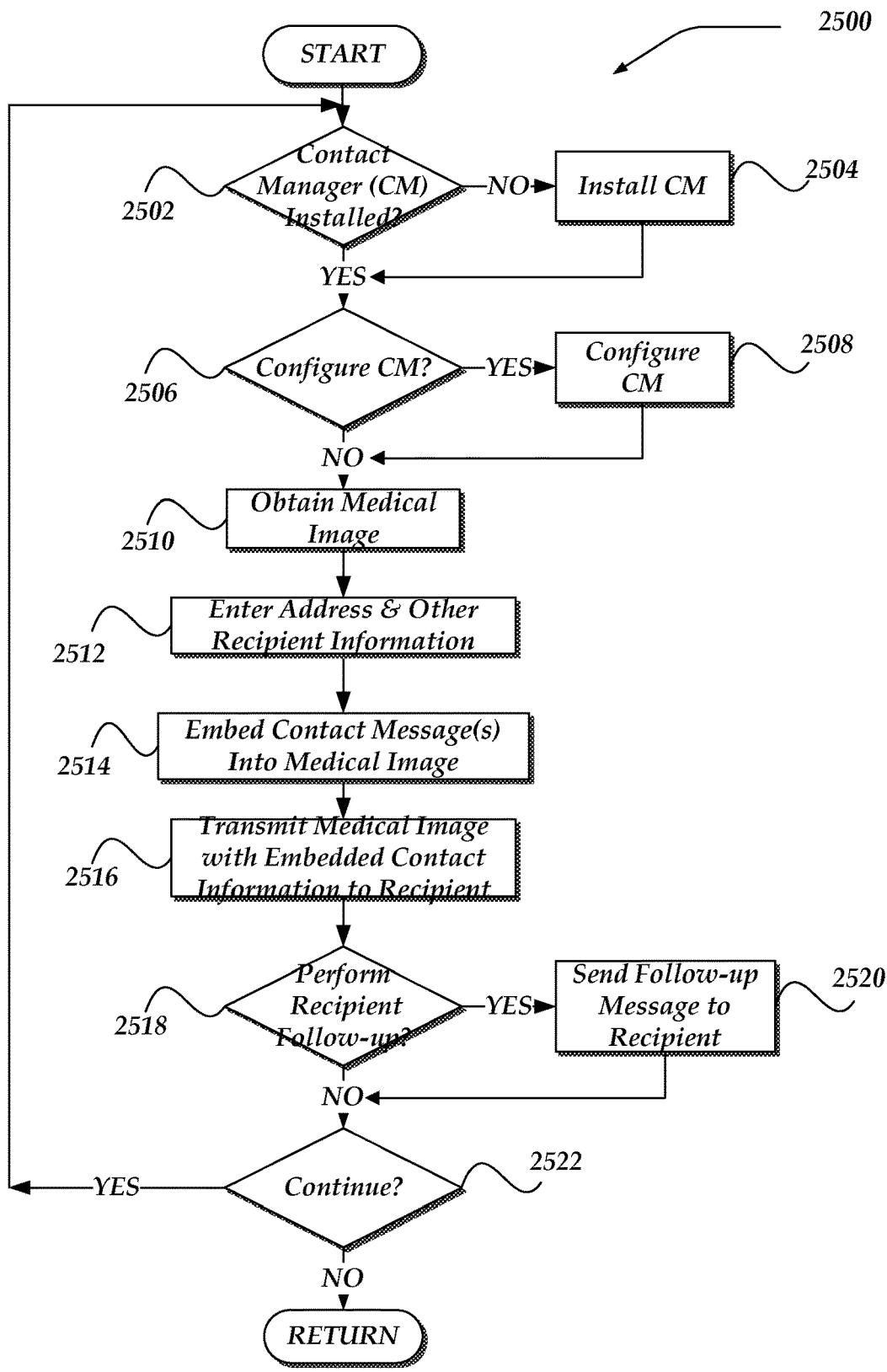

FIG. 25 illustrates a logical flow diagram generally showing one embodiment of a process usable to generate and transmit contact messages embedded within a personalized image, such as a medical diagnostic image. Process 2500 of FIG. 25 may be implemented within one or more processors 202 of FIG. 2, and/or within contact device 2310 of FIG. 23.

Process 2500 begins, after a start block, at decision block 2502, where a determination is made whether a contact manager application is installed and ready for execution on a computing device, such as mentioned above. If the determination is negative, then processing proceeds to block 2504; otherwise, processing proceeds to decision block 2506. In some embodiments, decision block 2502 may also make a determination of whether an application revision or update is to be installed. If so, then processing may also flow to block 2504, and otherwise, to decision block 2506.

At block 2504, the contact manager application, and/or updates thereto, are installed and readied for execution within one or more processors. In some embodiments, readying the application for execution might include configuring interfaces to a diagnostic imaging system, devices, applications, or the like. Flow then continues to decision block 2506.

At decision block 2506, a determination is made whether to configure the contact manager (CM) application with information about the professional, administrator, or other 'user' information. If such 'user' information is to be provided to the CM application, processing flows to block 2508; otherwise, processing continues to block 2510.

At block 2508, various user information is provided to the CM application, including address information about the user, or professional; network mailing information for sending patient information to a professional's office computing device; a phone number; fax number; and the like. In addition, the user may provide contact message information that may be embedded within a digital image. For example, the user might identify a number of contact messages to be embedded, and where to place the contact messages within an image. The user may further identify various hyperlink information, including, a link to the professional's website; a link to a coupon, advertisement, or other information useable by a patient; or a link usable for contacting the professional's office for follow-up care. The information included within a contact message may also be customized to allow advertising of special offers, holiday specials, or any of a variety of other information that the professional might wish to send to a patient.

Process 2500 then flows to block 2510, where a digital image is received. In one embodiment, the digital image is a medical diagnostic image, such as an image from a soft-tissue-injury diagnostic system, or other medical imaging system. Processing then flows to block 2512.

At block 2512, a patient's name, electronic mailing address, any "carbon copy" (cc) address information, information about the diagnostic analysis performed, any reply messages that might be unique to this patient, the professional's reply address information, or the like, may be entered. In one embodiment, a "reply to" address entered by the professional might be configured to redirect actual replies by the patient to the professional's office, or other identified address. It should be noted that block 2512 may also be performed prior or concurrent with block 2510.

Proceeding to block 2514, process 2500 employs the received information to generate one or more contact messages that may then be embedded into the digital image obtained at block 2510. Any of a variety of techniques may be used to embed the one or more contact messages, including various watermarking techniques, layering techniques, substitution techniques, or the like, where the one or more contact messages are visible, or otherwise accessible to a recipient. As noted above, one or more of the embedded contact messages may include a link, such as a hyperlink, or other selectable icon, or mechanism that is configured to enable the recipient to select the link. Selection of the link may then result in accessing the professional's website, dialing a phone number, accessing a coupon, or other information usable by the recipient.

Moreover, the information within the contact messages may include a variety of information. As non-limiting, non-exhaustive examples, a contact message might include information about a food drive at the professional's office, whereby the message indicates that if the message recipient, friends, or family 'brings a can of food to your office, they will receive a free diagnostic scan.' Another message might indicate that if the recipient responds by a selected date, by bringing their image results to the office by the selected date, they will receive some discounted service. Other messages may be included instead, or as well. In any event, it should be understood that that professional may include any of a variety of messages embedded within the digital image that might be useable to communicate the professional's services and to enhance a likelihood that the patient will return for additional care by the professional. Thus, the messages may be configured as 'that follow-up call to a patient that the professional wishes they could make.'

The contact messages may also include other forms beyond hyperlinks. For example, in some embodiments, a Quick Response (QR) Coded message might be embedded into the image. In some embodiments, the QR Code might then include a link to a website, or the like. However, still other mechanisms may be used that include audio and/or video content encoded within the one or more contact messages. In such embodiments, selection of these encodings enables an audio or video to be played absent linking to a website, or other network location.

In any event, continuing to block 2516, the digital image modified with the embedded one or more contact messages is transmitted to the recipient. In one embodiment, children's images might be sent to their parents or custodians, so that they may see why their children might need to have follow-up care. In some embodiments, the modified image with the embedded one or more contact messages could be electronically sent to a mobile device of the patient, even before they leave the professional's presence. The patient receiving the modified message may then be encouraged to forward this electronic contact message, or 'business card' to others through various social networking sites, email it to their friends, family, and other, thereby virally marketing the professional's business. That is, by encouraging the patient to share the modified image with one or more contact messages with others, the professional's business may be freely advertised, allowing the professional to appear as a 'high technology' professional.

In one embodiment, the modified message with one or more contact messages, and/or other information about the patient, may also be transmitted to the professional's office computing device, where follow-up calls, reminders, or the like, might be scheduled.

It should be noted, that in some situations, for any of a variety of reasons, a connection to a network might not be currently available for transmitting the messages, to the professional's office, and/or to the patient. In such situations, the modified message with one or more contact messages, and/or other information to be transmitted over a network may be stored, and when it is determined that a network connection is available, or based on some other criteria, the messages and/or other information can be automatically sent. In this manner, tests can be performed without a network connection to the patient or office, and the information can be sent at some later time.

Process 2500 continues to decision block 2518, where, in some embodiments, a determination is made whether to perform a patient follow-up contact. This might be based on any of a variety of criteria, including an elapsed time, consent to do so from the patient, a special event offering by the professional, or the like. In one embodiment, this action might be performed at the professional's office network device, such as network device 2305 of FIG. 1. However, in other embodiments, this action might be performed by contact device 2310 of FIG. 23. If a follow-up message is to be sent to the patient, processing flows to block 2520 where patient information may be used to send a follow-up message. Processing then flows to decision block 2522, from block 2520, or based on a negative determination at decision block 2518.

At decision block 2522, a determination is made whether to continue process 2500. If the process is to be continued, then flow branches back to decision block 2502; otherwise, processing may return to a calling process.

It will be understood that figures, and combinations of steps in the flowchart-like illustrations, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer implemented process such that the instructions, which execute on the processor to provide steps for implementing the actions specified in the flowchart block or blocks. These program instructions may be stored on a computer readable medium or machine readable medium, such as a computer readable storage medium.

Accordingly, the illustrations support combinations of means for performing the specified actions, combinations of steps for performing the specified actions and program instruction means for performing the specified actions. It will also be understood that each block of the flowchart illustration, and combinations of blocks in the flowchart illustration, can be implemented by modules such as special purpose hardware based systems which perform the specified actions or steps, or combinations of special purpose hardware and computer instructions.

Figure 26:
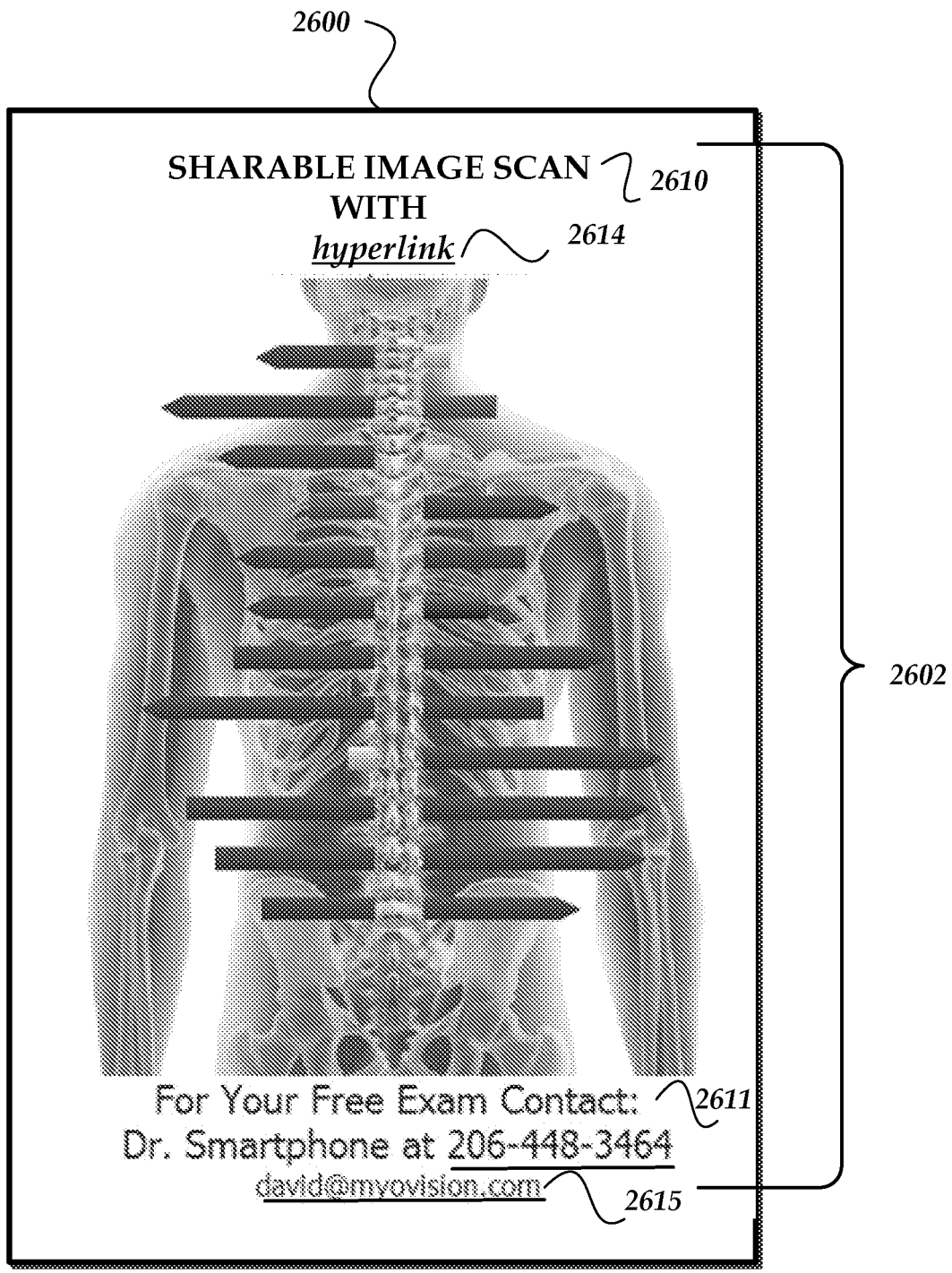
FIG. 26 shows one non-limiting, non-exhaustive example of a medical diagnostic image personalized with embedded contact messages, according to the invention.

Non-Limiting, No-Exhaustive Example of a Digital Image with Embedded Contact Messages FIG. 26 shows one non-limiting, non-exhaustive example of a modified image having embedded therein contact messages.

In any event, not all the components shown in FIG. 26 may be required to practice the embodiments and variations in the arrangement and type of the components may be made without departing from the scope of the invention. Moreover, various implementations of the modified image 2600 of FIG. 26 may include many more or less components than those shown. However, the components shown are sufficient to disclose an illustrative embodiment for practicing the present invention.

For example, while modified image 2600 of FIG. 26 discloses a medical diagnostic image 2602 that may be obtained from a soft-tissue-injury imaging device, other types of images may also be included. For example, as illustrated medical diagnostic image 2602 represents a Static sEMG result. Thus, images such as those obtained in motion, such as a Dynamic sEMG and Range of Motion images, might be included. Further, it should be understood that while a single image is shown, in other embodiments, a plurality of images might be included.

Moreover, as noted elsewhere, the digital image need not be medically related. For example, the image might be obtained for legal services, educational services, governmental services, or the like.

In any event, as shown, modified image 2600 includes medical diagnostic image 2602, and contact messages 2610-2611. As noted, contact messages 2610-2611 are shown embedded within a 'header' location of modified image 2600 and a 'footer' location. However, in other embodiments, one of more of contact messages 2610-2611 might be in a side location, such as to a right or left of medical diagnostic image 2602.

As used herein, the terms, header, footer, and side location, are directed towards identifying physical locations within the image, that might not obscure medical diagnostic image 260, itself, rather than locations that might be outside of a digital image data region. Thus, embedding of the contact messages result in modifying the image, rather than merely adding content to regions outside of the image. For example, as shown in FIG. 26, contact messages 2610-2611 are within the region identified with the digital data image, but are located above/below the visible portion of medical diagnostic image 2602. However, in some embodiments, contact messages 2610-2611 might obscure at least a portion of the medical diagnostic image 2602.

As noted, modified image 2600 need not have two contact messages. For example, one contact message, or a plurality of contact messages might be included. Moreover, while contact messages 2610-2611 are not shown as covering or obfuscating medical diagnostic image 2602, in other embodiments, one or more contact messages could be so placed to cover or obscure at least a portion of the digital image.

As illustrated contact message includes a selectable hyperlink 2614 to any of a variety of information, including, but not limited to a professional's website, professional's office, or the like. For example, as shown, contact message 2611 includes selectable links to a phone number 2611 and an email address 2615. Selection of any of the included links enable the patient to then dial a phone number, email a message, or access a webpage, or other information. For example, hyperlink 2614 might be a link that accesses a coupon, an advertisement, more information about the professional's business, information about the medical diagnostic image 2602, or the like. In one embodiment, selection of hyperlink 2614 might be configured to contact the professional's office to schedule a follow-up session.

As noted above, contact messages 2610-2611 might include a QR Code, or other mechanism usable to link to a website, or to embed an audio or video sequence within the modified image 2600.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A computing system, comprising:
   a set of hand-held inclinometers for marking and recording measured angles at one or more of a first position and a second position for a joint of a patient's body;
   a surface electromyograph ("sEMG") module and a set of measuring electrodes that measure action potentials monitored externally along one or more patient muscle groups of the patient's body; and
   one or more ground electrodes that are placed against patient skin adjacent to the set of measuring electrodes, wherein the one or more ground electrodes and the set of measuring electrodes are physically located together in a housing, and wherein the one or more ground electrodes are retractable when pressed to a compressed position against the patient's skin, within the same housing, independently of the set of measuring electrodes, wherein the one or more ground electrodes are retractable to improve simultaneous contact with the patient's skin between the sEMG module and the set of measuring electrodes and the one or more ground electrodes pressed against the patient skin on the exterior of the patient's body, and wherein the one or more ground electrodes are configured in an uncompressed position that extends beyond a surface of the housing and also beyond a position of the set of measuring electrodes until the one or more ground electrodes retract from the extended position to the compressed position that is closer to the surface of the housing and one or more tips of the set of measuring electrodes when the set of measuring electrodes and the one or more ground electrodes are pressed against the patient skin, and wherein a tip of each of the one or more retractable ground electrodes and each tip of the set of the measuring electrodes are pivotable from each other tip to maintain contact with contours of the patient's body and skin on the outside of the patient's body, and wherein action potential signals are actively monitored by and data is collected from the inclinometers and the sEMG module for subsequent processing into digital image data; and
   a computing device that includes one or more processors configured to execute software to perform actions, including:
      installing a contact manager application on the computing device, wherein execution of the contact manager application configures one or more user interfaces based on one or more of the computing system, other applications, and selected contact information for a medical professional;

idling the software of the computing device until the patient's body is detected in a final neutral position; and in response to detection of the final neutral position, emitting a voice signal to perform actions, comprising:

marking a current position of the set of hand-held inclinometers when a user is performing a range of motion (ROM) evaluation of the patient while monitoring the action potentials measured externally along one or more patient muscle groups of the patient's body; and providing voice commands to instruct the patient to perform a given movement during their ROM evaluation; and employing a completed ROM evaluation of the patient and the monitored action potentials to automatically determine if the completed ROM evaluation is invalid and determine a correspondence to a nature and an extent of an injury to the patient's body or tracking progress of the injury over time.

2. The computing system of claim 1, wherein the selected contact information includes a selectable link that when selected is configured to contact the medical professional.

3. The computing system of claim 1, wherein the selected contact information includes at least one of an advertisement or coupon information usable to obtain a discounted service from the medical professional.

4. The computing system of claim 1, wherein the further modified digital image data is configured to include at least one selectable phone number or email address of the medical professional.

5. The computing system of claim 1, wherein the one or more processors are configured to perform actions, further including:

sending to a network device associated with the medical professional, patient contact information about a patient associated with the medical diagnostic image.

6. The computing system of claim 1, wherein the selected contact information for the medical professional includes at least one of a Quick Response (QR) Code, an audio clip, or a video clip that is selectable by a recipient of the further modified digital data image.

7. The system of claim 1, further comprising:

the computing device that includes one or more processors configured to perform further actions, including receiving digital image data for a medical diagnostic image;

modifying the digital image data by deleting from within the received digital image data private patient information;

selecting contact information for a medical professional associated with the received medical diagnostic image;

further modifying the digital image data by embedding the selected contact information into the modified digital image data for the medical diagnostic image, wherein a non-transitory computer readable medium is configured and arranged to store the further modified digital image data;

electronically sending the further modified digital image data and embedded selected contact information over a network, wherein the further modified digital image data is retrieved from the non-transitory computer readable medium; and posting the modified digital image data to at least one social networking site.

8. An apparatus, comprising:

a set of hand-held inclinometers for marking and recording measured angles at one or more of a first position and a second position for a joint of a patient's body;

a surface electromyograph ("sEMG") module and a set of measuring electrodes that measure action potentials monitored externally along one or more patient muscle groups of the patient's body; and one or more ground electrodes that are placed against patient skin adjacent to the set of measuring electrodes, wherein the one or more ground electrodes and the set of measuring electrodes are physically located together in a housing, and wherein the one or more ground electrodes are retractable when pressed to a compressed position against the patient's skin, within the same housing, independently of the set of measuring electrodes, wherein the one or more ground electrodes are retractable to improve simultaneous contact with the patient's skin between the sEMG module and the set of measuring electrodes and the one or more ground electrodes pressed against the patient skin on the exterior of the patient's body, and wherein the one or more ground electrodes are configured in an uncompressed position that extends beyond a surface of the housing and also beyond a position of the set of measuring electrodes until the one or more ground electrodes retract from the extended position to the compressed position that is closer to the surface of the housing and one or more tips of the set of measuring electrodes when the set of measuring electrodes and the one or more ground electrodes are pressed against the patient skin, and wherein a tip of each of the one or more retractable ground electrodes and each tip of the set of the measuring electrodes are pivotable from each other tip to maintain contact with contours of the patient's body and skin on the outside of the patient's body, and wherein action potential signals are actively monitored by and data is collected from the inclinometers and the sEMG module for subsequent processing into digital image data; and a computing device that includes one or more processors configured to execute software to perform actions, including:

installing a contact manager application on the computing device, wherein execution of the contact manager application configures one or more user interfaces based on one or more of the apparatus, other applications, and selected contact information for a medical professional;

idling the software of the computing device until the patient's body is detected in a final neutral position; and in response to detection of the final neutral position, emitting a voice signal to perform actions, comprising:

marking a current position of the set of hand-held inclinometers when a user is performing a range of motion (ROM) evaluation of the patient while monitoring the action potentials measured externally along one or more patient muscle groups of the patient's body; and providing voice commands to instruct the patient to perform a given movement during their ROM evaluation; and employing a completed ROM evaluation of the patient and the monitored action potentials to automatically determine if the completed ROM evaluation is invalid and determine a correspondence to a nature and an extent of an injury to the patient's body or tracking progress of the injury over time.

9. The apparatus of claim 8, wherein sharing of the modified digital image data with the embedded selected contact information comprises posting to a social networking site, or emailing the modified digital image data with the embedded selected contact information to at least one other computing device.

10. The apparatus of claim 8, wherein the selected contact information includes a selectable link that when selected is configured to contact the medical professional.

11. The apparatus of claim 8, wherein the selected contact information includes information usable to obtain a discounted service from the medical professional.

12. The apparatus of claim 8, wherein the further modified digital image data is configured to include at least one selectable phone number or email address of the medical professional that when selected, performs actions to contact the medical professional.

13. The apparatus of claim 8, further comprising:
sending to a network device associated with the medical professional, patient contact information about the patient, the patient contact information being configured to enable a follow-up session to be scheduled with the patient.

14. The apparatus of claim 8, further comprising:
the computing device that includes one or more processors that execute the instructions to perform further actions, including:
receiving digital image data for a medical diagnostic image of a patient;
modifying the digital image data by deleting private patient information;
selecting contact information for a medical professional associated with the received medical diagnostic image;
embedding the selected contact information into the modified digital image data for the medical diagnostic image, wherein the non-transitory computer readable medium is configured and arranged to store the modified digital image data that includes the embedded selected contact information; and
electronically sending the modified digital image data with the embedded selected contact information over a network to the patient, wherein the modified digital image data that includes the embedded selected contact information is retrieved from the non-transitory computer readable medium.

15. A system, comprising:
a set of hand-held inclinometers for marking and recording measured angles at one or more of a first position and a second position for a joint of a patient's body;
a surface electromyograph ("sEMG") module and a set of measuring electrodes that measure action potentials monitored externally along one or more patient muscle groups of the patient's body; and
one or more ground electrodes that are placed against patient skin adjacent to the set of measuring electrodes, wherein the one or more ground electrodes and the set of measuring electrodes are physically located together in a housing, and wherein the one or more ground electrodes are retractable when pressed to a compressed position against the patient's skin, within the same housing, independently of the set of measuring electrodes, wherein the one or more ground electrodes are retractable to improve simultaneous contact with the patient's skin between the sEMG module and the set of measuring electrodes and the one or more ground electrodes pressed against the patient skin on the exterior of the patient's body, and wherein the one or more ground electrodes are configured in an uncompressed position that extends beyond a surface of the housing and also beyond a position of the set of measuring electrodes until the one or more ground electrodes retract from the extended position to the compressed position that is closer to the surface of the housing and one or more tips of the set of measuring electrodes when the set of measuring electrodes and the one or more ground electrodes are pressed against the patient skin, and wherein a tip of each of the one or more retractable ground electrodes and each tip of the set of the measuring electrodes are pivotable from each other tip to maintain contact with contours of the patient's body and skin on the outside of the patient's body, and wherein action potential signals are actively monitored by and data is collected from the inclinometers and the sEMG module for subsequent processing into digital image data; and
a computing device that includes one or more processors configured to execute software to perform actions, including:
installing a contact manager application on the computing device, wherein execution of the contact manager application configures one or more user interfaces based on one or more of the system, other applications, and selected contact information for a medical professional;
idling the software of the computing device until the patient's body is detected in a final neutral position; and
in response to detection of the final neutral position, emitting a voice signal to perform actions, comprising:
marking a current position of the set of hand-held inclinometers when a user is performing a range of motion (ROM) evaluation of the patient while monitoring the action potentials measured externally along one or more patient muscle groups of the patient's body; and
providing voice commands to instruct the patient to perform a given movement during their ROM evaluation; and
employing a completed ROM evaluation of the patient and the monitored action potentials to automatically determine if the completed ROM evaluation is invalid and determine a correspondence to a nature and an extent of an injury to the patient's body or tracking progress of the injury over time.

16. The apparatus of claim 15, wherein the embedded contact information includes at least one selectable phone number or email address of the professional that when selected, performs actions to contact the professional.

17. The apparatus of claim 15, wherein the computing device having one or more processors configured to perform actions, further including:
sending to a network device associated with the professional, client contact information about the client usable to enable a follow-up session to be scheduled with the client.

18. The apparatus of claim 15, wherein the embedded selected contact information further includes information useable to obtain a discounted service from the professional.

19. The apparatus of claim 15, further comprising posting the modified digital diagnostic image with the embedded selected contact information on a social networking site or on a messaging system.

20. The System of claim 15, further comprising:
- an imaging device usable to generate a digital diagnostic image associated with a client; and
- the computing device having one or more processors configured to perform further actions, including:
  - receiving the generated digital diagnostic image;
  - modifying the digital diagnostic image by removing private client information within the digital diagnostic image;
  - selecting contact information for a medical professional associated with the received digital diagnostic image;
  - embedding the selected contact information into the modified digital image data for the medical diagnostic image, wherein a non-transitory computer readable medium is configured and arranged to store the modified digital image data that includes the embedded selected contact information; and
- electronically sending the modified digital image data with the embedded selected contact information over a network to the client, wherein the modified digital image data that includes the embedded selected contact information is retrieved from the non-transitory computer readable medium.

* * * * *